(12) United States Patent
Nobis

(10) Patent No.: US 9,526,518 B2
(45) Date of Patent: Dec. 27, 2016

(54) SURGICAL CUTTING DEVICES AND METHODS THAT INCLUDE A SELF-ADJUSTING CUTTING BLADE

(71) Applicant: Ethicon Endo-Surgery, LLC, Guaynabo, PR (US)

(72) Inventor: Rudolph H. Nobis, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 117 days.

(21) Appl. No.: 14/229,456

(22) Filed: Mar. 28, 2014

(65) Prior Publication Data

US 2015/0272606 A1 Oct. 1, 2015

(51) Int. Cl.
| | | |
|---|---|---|
| A61B 17/3205 | (2006.01) | |
| A61B 17/3201 | (2006.01) | |
| A61B 18/14 | (2006.01) | |
| A61B 18/00 | (2006.01) | |

(52) U.S. Cl.
CPC ....... *A61B 17/3201* (2013.01); *A61B 18/1445* (2013.01); *A61B 2018/0063* (2013.01); *A61B 2018/1455* (2013.01); *A61B 2018/1457* (2013.01); *A61B 2560/04* (2013.01)

(58) Field of Classification Search
CPC ............. A61B 17/3205; A61B 17/320016; A61B 17/28; A61B 17/122; A61B 2560/04; A61B 10/06; A61B 17/32; A61B 17/32113; A61B 17/320092; A61B 17/3201; A61B 10/02; A61B 10/0233; A61B 17/29; A61B 17/3207; A61B 17/14; A61B 18/1445; A61B 2018/1455; A61B 18/085; A61B 17/282; A61B 17/295; A61B 17/285; A61B 17/1227; A61B 17/12; A61F 9/00763; B26B 17/00; B26B 13/22; B26D 29/02–29/026
USPC ........ 606/169, 170, 174, 205, 213, 210, 120
See application file for complete search history.

(56) References Cited

U.S. PATENT DOCUMENTS

| | | | |
|---|---|---|---|
| 3,826,160 A | * | 7/1974 | Allen .................... A01K 11/002 29/238 |
| 5,599,350 A | | 2/1997 | Schulze et al. |
| 5,984,938 A | * | 11/1999 | Yoon ................ A61B 17/12013 606/139 |
| 6,168,605 B1 | * | 1/2001 | Measamer ..... A61B 17/320016 606/170 |
| 8,298,232 B2 | | 10/2012 | Unger |

(Continued)

*Primary Examiner* — David C Eastwood
*Assistant Examiner* — Mikail Mannan
(74) *Attorney, Agent, or Firm* — Nutter McClennen & Fish LLP

(57) ABSTRACT

Devices and methods for cutting tissue are provided, and more particularly the devices and methods provide for ways to prevent a cutting blade from becoming dislodged or otherwise disassociated from jaws of a surgical device. In one exemplary embodiment, a surgical device includes a jaw assembly having first and second jaws and a cutting blade. The cutting blade can include a spring mechanism configured to engage a portion of the second jaw to bias a cutting edge of the cutting blade towards the first jaw such that a top of the cutting blade distal portion contacts a portion of the first jaw. In another exemplary embodiment, a biasing block is included as part of a surgical instrument to help maintain distal ends of two cutting blades hooked against each other to form a single cutting surface. Other devices and methods for cutting tissue are also provided.

17 Claims, 14 Drawing Sheets

(56) References Cited

U.S. PATENT DOCUMENTS

| | | | |
|---|---|---|---|
| 8,568,412 B2 * | 10/2013 | Brandt | A61B 18/1445 |
| | | | 606/205 |
| 2006/0161190 A1 * | 7/2006 | Gadberry | A61B 17/1608 |
| | | | 606/174 |
| 2012/0083835 A1 | 4/2012 | Shelton, IV et al. | |
| 2013/0161374 A1 | 6/2013 | Swayze et al. | |
| 2015/0190191 A1 | 7/2015 | Strobl | |

* cited by examiner

SURGICAL CUTTING DEVICES AND METHODS THAT INCLUDE A SELF-ADJUSTING CUTTING BLADE

FIELD

The present invention relates to surgical devices and methods for transecting or cutting tissue, and more particularly to one or more cutting blades having one or more self-adjusting features to help maintain the blade(s) in a desired location.

BACKGROUND

Surgical devices are used in various open, endoscopic, and laparoscopic surgeries to transect tissue volumes and blood vessels. The devices generally include jaws for grasping tissue therebetween and a cutting mechanism that is advanced through the grasped tissue to transect it. The cutting mechanism can be designed to travel within a track formed in one or both jaws of the cutting mechanism. In some instances the devices can also be used to seal tissue volumes and blood vessels being transected, for instance by applying electrical energy to the grasped tissue to seal it before tissue transection is completed. For example, various mono-polar and bi-polar radio frequency (RF) surgical instruments and surgical techniques have been developed for sealing tissue volumes and blood vessels. Electrodes can be disposed on a face of one or both of the jaws and can apply energy to the grasped tissue to promote hemostasis.

One issue that can plague tissue cutting devices is that the cutting mechanism may become dislodged or may otherwise fall out of a track formed in one or both of the jaws. The likelihood of the cutting mechanism becoming dislodged in current cutting devices typically increases as the thickness of the tissue volume or blood vessel being transected by the device increases. This is because a thicker tissue can cause the jaws to be open too wide such that the cutting mechanism becomes displaced from the track(s).

Accordingly, there remains a need for improved surgical devices that help to maintain a desired location of a cutting mechanism even in the presence of thicker tissue or blood vessels.

SUMMARY

Devices and methods are generally provided for cutting volumes of tissue and blood vessels. In one exemplary embodiment, a surgical instrument includes a jaw assembly and a cutting blade. The jaw assembly can include a first jaw and a second jaw pivotally coupled together, with the first and second jaws having opposed tissue contacting surfaces configured to pivot towards each other to engage tissue therebetween. The cutting blade can have a distal portion that is disposed between the opposed tissue contacting surfaces of the jaws. The distal portion can include a terminal, vertically disposed cutting edge that extends between the first and second jaws. Further, the distal portion can include a spring mechanism configured to engage a portion of the second jaw to bias the cutting edge towards the first jaw such that a top of the distal portion of the cutting blade contacts a portion of the first jaw.

The cutting blade can be configured to translate axially through a portion of the first and second jaws in a distal direction to cut tissue disposed between the first and second jaws. A vertical height of the cutting edge can be greater than a distance between the opposed tissue contacting surfaces of the first and second jaws at equivalent axial locations as the cutting blade translates axially through a portion of the first and second jaws. In some embodiments, a pusher can be coupled to a proximal portion of the cutting blade. The pusher can be configured to translate the cutting blade axially through a portion of the first and second jaws.

The spring mechanism can include an elongate flexing arm that can be configured to flex about a pivot point located on the cutting blade. In some embodiments, the pivot point can be distal of the elongate flexing arm. Further, in some embodiments, the pivot point can be located adjacent to the terminal, vertically disposed cutting edge, at a location that is more proximate to the second jaw than the first jaw.

The first and second jaws can have opposed channels disposed therein. A portion of the distal portion of the cutting blade can be disposed in each of the opposed channels.

In another exemplary embodiment of a surgical instrument, the instrument can include a jaw assembly, a first cutting blade, a second cutting blade, and a biasing block. The jaw assembly can include first and second jaws that are pivotally coupled together, with each of the jaws having an axial channel extending through a portion thereof. The first and second jaws can generally be configured to engage tissue therebetween. The first cutting blade can have a portion thereof disposed in the axial channel of the first jaw, and the second cutting blade can have a portion thereof disposed in the axial channel of the second jaw. Each of the first and second cutting blades can have a proximal end, a distal end, a first side surface, and a second side surface, with the distal end of each blade being configured to cut tissue disposed between the first and second jaws. An intermediate portion of the first side surface of the first cutting blade can be adjacent to and opposed to an intermediate portion of the first side surface of the second cutting blade. Further, proximal ends of the first and second cutting blades can be disposed in the biasing block and the distal ends of the two cutting blades can be hooked against each other such that the second side surface of the first cutting blade is in contact with the second side surface of the second cutting blade. The distal ends can be maintained in this hooked against position by the bias supplied by the proximal ends of the cutting blades being disposed in the biasing block.

Other embodiments can include the distal ends of the two cutting blades being disposedly biased together and distally hooked together, and with the disposing bias force introduced by a separation block transported between the two blades.

In some embodiments, the axial channels of the first and second jaws can be substantially centrally disposed with respect to a width of the respective first and second jaws. The biasing block can bias the distal ends of the first and second cutting blades such that the cutting blades are approximately centrally disposed within the axial channels of the respective first and second jaws.

The biasing block can include a first receiving block and a second receiving block. The first receiving block can have a slot disposed therein, the slot being configured to receive the proximal end of the first cutting blade. The second receiving block can be pivotally coupled to the first receiving block, and can likewise have a slot disposed therein that is configured to receive the proximal end of the second cutting blade. The slot of the first receiving block can extend at a first angle with respect to a central longitudinal axis extending between the first and second jaws. Further, the slot of the second receiving block can extend at a second angle with respect to the central longitudinal axis. In some embodiments, the first and second angles can have substantially similar values, with the first angle extending in a first direction away from the central longitudinal axis and the second angle extending in a second direction away from the central longitudinal axis, the first and second directions being opposed to each other. In some embodiments, the first and second angles can have values in the range of greater than 0 degrees to about 10 degrees.

Distal ends of the first and second cutting blades can overlap to form a cutting surface to cut tissue disposed between the first and second jaws. In some embodiments, one or more biasing elements can be coupled to the first and second cutting blades, and the one or more biasing elements can be configured to bias the first cutting blade towards a base of the axial channel of the first jaw and to bias the second cutting blade towards a base of the axial channel of the second jaw. In some embodiments, the axial channels of the first and second jaws can be curved with respect to a central longitudinal axis extending between the first and second jaws.

One exemplary surgical method includes clamping tissue between opposed first and second jaws of a surgical instrument and distally advancing a cutting blade of the surgical instrument through a portion of the opposed first and second jaws to cut the clamped tissue to perform a cutting stroke. A terminal, vertically disposed cutting edge of the cutting blade can be disposed within a portion of the second jaw and can be in contact with a portion of the first jaw during a substantial entirety of the cutting stroke due to a spring bias supplied to the cutting blade.

In some embodiments the spring bias can be supplied at a location proximate to a distal end of the cutting blade, while in other embodiments the spring bias can be supplied at a proximal end of the cutting blade. Further, in some embodiments, the spring bias can be supplied by a spring member formed in a portion of the cutting blade. The method can further include distally advancing a second cutting blade of the surgical instrument through a portion of the opposed first and second jaws to cut the clamped tissue. A terminal, vertically disposed cutting edge of the second cutting blade can be adjacent to the terminal, vertically disposed cutting edge of the first cutting blade to form a single cutting surface. In some embodiments, a portion of the surgical instrument can be configured to apply a force to proximal ends of the first and second cutting blades to provide a bias that aids in maintaining distal ends of the first and second cutting blades hooked together to form the single cutting surface.

BRIEF DESCRIPTION OF DRAWINGS

This invention will be more fully understood from the following detailed description taken in conjunction with the accompanying drawings, in which.

DETAILED DESCRIPTION

Figure 1:
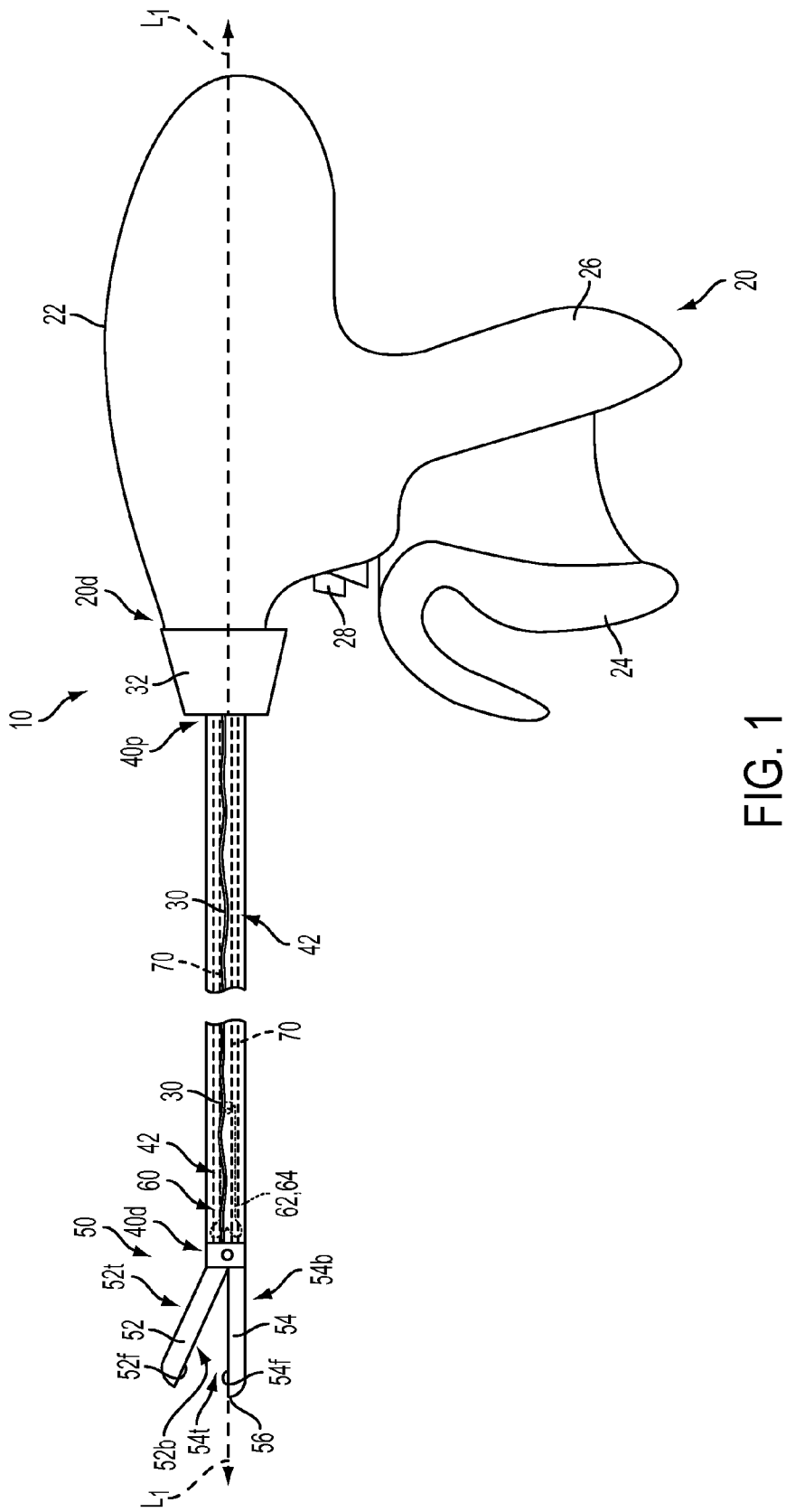
FIG. 1 is a side view of one exemplary embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the various embodiments generally have similar features when those components are of a similar nature and/or serve a similar purpose. Additionally, to the extent features or sides of a structure are described herein as being a "first feature" or "first side" or a "second feature" or "second side," such numerical ordering is generally arbitrary, and thus such numbering can be interchangeable.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Further, a person skilled in the art will recognize that a number of different terms can be used interchangeably while still being understood by the skilled person. By way of non-limiting example, the terms "cut" and "transect" are generally used interchangeably herein.

The present disclosure generally relates to surgical devices and methods for transecting tissue or blood vessels, collectively referred to herein as "tissue." The devices, also referred to herein as instruments, disclosed or otherwise derivable from the disclosures herein include various features for biasing a cutting mechanism of a device towards a desired location to help maintain its location with respect to jaws of the device. For example, the jaws can include a track or axial channel formed therein through which the cutting mechanism can axially travel, and the features provided for herein can help maintain the cutting mechanism within the track. In some instances, the cutting mechanism can be a single cutting blade effective to transect tissue disposed between the jaws. In alternative embodiments, the cutting mechanism can include multiple cutting blades that are effective to transect tissue disposed between the jaws. In embodiments that includes multiple cutting blades, the blades can interact together as a single cutting surface to help limit the possibility of tissue becoming trapped between the blades.

The disclosures provided for herein provide biasing of the cutting mechanism in at least two different planes. As shown in FIG. 1, in some embodiments of a device 10, a cutting mechanism 60 is configured to be biased in a first plane that is co-planar with the page. The first plane extends vertically such that it substantially bisects each of the first and second jaws 52, 54. In other words, the cutting mechanism 60 is biased towards at least one of a top surface 52t and a bottom surface 54b of the respective first and second jaws 52, 54. In embodiments in which the cutting mechanism 60 includes a single blade, the blade can be biased towards one of the surfaces 52t, 54b of the jaws 52, 54, while in embodiments in which the cutting mechanism 60 includes two blades 62, 64, one blade 62 can be biased towards one of the surfaces 52t, 54b while the other blade 64 can be biased towards the other surface 52t, 54b. Biasing blades 62, 64 of the cutting mechanism 60 towards one or both surfaces 52t, 54b of the jaws 52, 54 can help maintain a location of the blade(s) with respect to the jaws 52, 54, and thus enables the blade(s) to be self-adjusting as it translates through the jaws 52, 54.

A cutting mechanism 60 that includes two cutting blades 62, 64 can also be configured such that the two blades 62, 64 are biased towards each other in a second plane that is substantially perpendicular to the first place, i.e., the second plane extends into and out of the page such that it extends substantially parallel to opposed tissue contacting surfaces 52f, 54f of the jaws 52, 54 when the jaws 52, 54 are in a closed position. In other words, the two cutting blades 62, 64 can be biased towards each other and towards the central longitudinal axis $L_1$. Track 52c, 54c (FIG. 2) can be disposed in either or both of the jaws 52, 54, aligned with the central longitudinal axis $L_1$, such that the biased cutting blades 62, 64 are biased to remain approximately centrally disposed within the tracks 52c, 54c. As a result, the blades can be self-adjusting to maintain their location with respect to the jaws 52, 54 as they translate through the jaws 52, 54.

Surgical Device

FIG. 1 illustrates one embodiment of a surgical device 10 configured to grasp, seal, and transect tissue. The surgical device can include a proximal handle portion 20, a shaft 40, and an end effector 50 for grasping tissue. The handle portion 20 can be designed to operate various features of the end effector 50. For example, the handle portion 20 can close and open a jaw assembly of the end effector 50 to grasp tissue. The jaw assembly can include jaws 52, 54 that are configured to pivot with respect to each other to grasp tissue disposed therebetween. By way of further non-limiting example, the handle portion 20 can initiate the supply of electrical energy to one or more electrodes 56 associated with either or both of the jaws 52, 54 to weld or otherwise seal portions of the grasped tissue. The components to initiate these actions can be part of the handle portion 20 and can extend through or be electrically or mechanically coupled to components that extend through the shaft 40. Components of this nature are known to those skilled in the art, and thus further elaboration related to the same is unnecessary. Further, the handle portion 20 can also be configured to operate other components that work in conjunction with the end effector 50, such as one or more cutting blades 62, 64 that extend through a portion of the shaft 40 and are configured to cut tissue grasped by the jaws 52, 54. In some embodiments, but not the illustrated embodiment, the cutting blades can also serve as a compression member by being configured to move the jaws 52, 54 from an open to a closed position, as known to those skilled in the art.

The handle portion 20 can have any type of design known in the art for operating end effectors 50. In the illustrated embodiment, the handle portion 20 has a pistol-grip configuration that includes a housing 22, an actuating handle 24, and a stationary handle 26. Movement of the actuating handle 24 towards the stationary handle 26 can be effective to perform a variety of functions. In the illustrated embodiment, the actuating handle 24 is effective to close the jaws 52, 54 and cut tissue disposed between the jaws. In some embodiments, the actuating handle 24 can move through two separate cycles or strokes to perform these functions. For example, the actuating handle 24 can move through a first cycle or stroke in which it first moves towards the stationary handle 26 and then returns back to its initial position, during which time its movement towards the stationary handle 26 is effective to close the jaws 52, 54. The actuating handle 24 can then move through a second cycle or stroke, again moving towards the stationary handle 26 and then returning back to its initial position, during which times its movement towards the stationary handle 26 is effective to pass the one or more cutting blades 62, 64 through at least a portion of the jaws 52, 54 to cut tissue disposed therebetween. While a variety of configurations can be used to allow movement of the actuating handle 24 to translate into distal movement of the one or more cutting blades 62, 64, as described in further detail below, the actuating handle 24 can be effective to distally advance an actuation rod or pusher 70 coupled to the one or more cutting blades 62, 64 such that axial movement of the actuation rod 70 in the distal and proximal directions results in axial movement of the cutting blades 62, 64 in distal and proximal directions as well. Accordingly, as the actuating handle 24 returns to the initial position during the second stroke, the one or more cutting blades 62, 64 can retract proximally with respect to the jaws 52, 54.

The mechanical and electrical components associating the actuating handle 24 with the jaws 52, 54 and or the one or more cutting blades 62, 64 can be disposed in the housing 22 and the shaft 40, including motors, controllers, and levers, among other components. Other designs that can be used to actuate the jaws 52, 54 and the one or more cutting blades 62, 64 include but are not limited to actuator levers, triggers, and sliders. Further, a person skilled in the art will recognize other functions that the actuating handle 24, or other means of actuation, can perform without departing from the spirit of the present disclosure.

The illustrated embodiment also includes an actuator, e.g. a button 28, as part of the handle portion 20. The button 28 can be configured such that pressing it completes a circuit to power the electrode(s) 56 to seal tissue disposed in the jaws 52, 54. More particularly, completion of the circuit by the button 28 allows electrical energy to pass from a power source disposed in the housing 22, through one or more electrical leads 30, and to the electrode 56. The electrical lead can be disposed in the shaft 40 to electrically connect the button 28 and the electrode 56. Although the power source is described as being in the housing 22, in other embodiments the power source can be external of the housing 22 and the housing can be configured to electrically connect to the power source, for instance by way of a socket extending from the housing 22 to connect to the power source. Similar to the actuating handle 24, a person skilled in the art will recognize that the actuator can have a variety of other designs, and can perform a variety of other types of functions, without departing from the spirit of the present disclosure.

Other features to assist in moving and actuating the components of the device 10 can also be incorporated into the handle portion 20. By way of example, the handle portion 20 can include a rotatable knob 32 disposed at a distal end 20d of the handle portion 20 to facilitate rotation of the shaft 40, and thus the end effector 50 coupled thereto, with respect to the handle portion 20 around a centrally disposed longitudinal axis $L_1$ of the shaft 40. A person skilled in the art will recognize other non-limiting examples of features that can be incorporated with the handle portion 20 to assist in manipulating or otherwise operating the device include: (1) an articulation lever for articulating the end effector 50; (2) a retraction handle for retracting the one or more cutting blades 62, 64 towards and/or to their initial positions in place of or independent of any retraction that is part of a firing stroke initiated by the actuating handle 24; (3) a firing lockout assembly to prevent the one or more cutting blades 62, 64 from being actuated at an undesirable time; and (4) an emergency return button to retract the one or more cutting blades 62, 64 before a firing stroke is completed, for instance in a case where completing the firing stroke may cause tissue to be undesirably cut. Although features such as an articulation lever, a retraction handle, a firing lockout assembly, and an emergency return button are not explicitly illustrated in the device 10, a person skilled in the art will recognize a variety of configurations for each feature that can be incorporated into the handle portion 20 and/or other portions of the device 10 without departing from the spirit of the present disclosure.

The shaft 40 can be removably coupled to the distal end 20d of the handle portion 20 at a proximal end 40p of the shaft 40 and can include a bore 42 extending therethrough for passing mechanisms to help actuate the jaws 52, 54, or to perform other functions at the surgical site, such as cutting or delivering electrical energy for sealing. In the described embodiment, the actuation rod 70, the one or more cutting blades 62, 64, and leads 30 are coupled to the components of the handle portion and extend through the shaft 40 to the end effector 50. A distal end 40d of the shaft 40 can be configured to receive the end effector 50 by any known means for coupling an end effector to a shaft, including by a removable connection that allows various end effectors to be removably and replaceably coupled to the distal end 40d. While the shaft 40 can have any number of shapes and configurations, depending, at least in part, on the configurations of the other device components with which it is used and the type of procedure in which the device is used, in the illustrated embodiment the shaft 40 is generally cylindrical and elongate.

The illustrated embodiment of a surgical stapling instrument 10 provides one of many different configurations, and associated methods of use, that can be used in conjunction with the disclosures provided herein. Additional exemplary embodiments of surgical staplers, components thereof, and their related methods of use, that can be used in accordance with the present disclosure include those devices, components, and methods provided for in U.S. Pat. No. 8,298,232, U.S. Patent Application Publication No. 2012/0083835 and U.S. Patent Application Publication No. 2013/0161374, each of which is incorporated by reference herein in its entirety. While the illustrated embodiment includes features for sealing tissue, in other embodiments the surgical device can be configured to grasp and cut tissue without including a sealing feature.

End Effector

Figure 2:
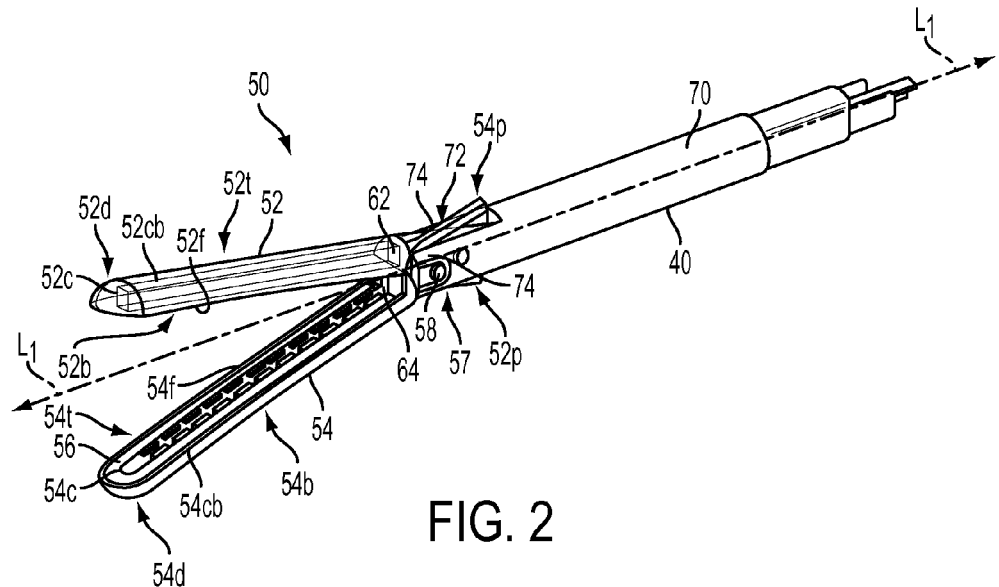
FIG. 2 is a partially transparent perspective view of an end effector and a shaft of the surgical device of FIG. 1, the end effector including first and second jaws disposed in an open position and first and second cutting blades disposed in a proximal location.
Figure 3:
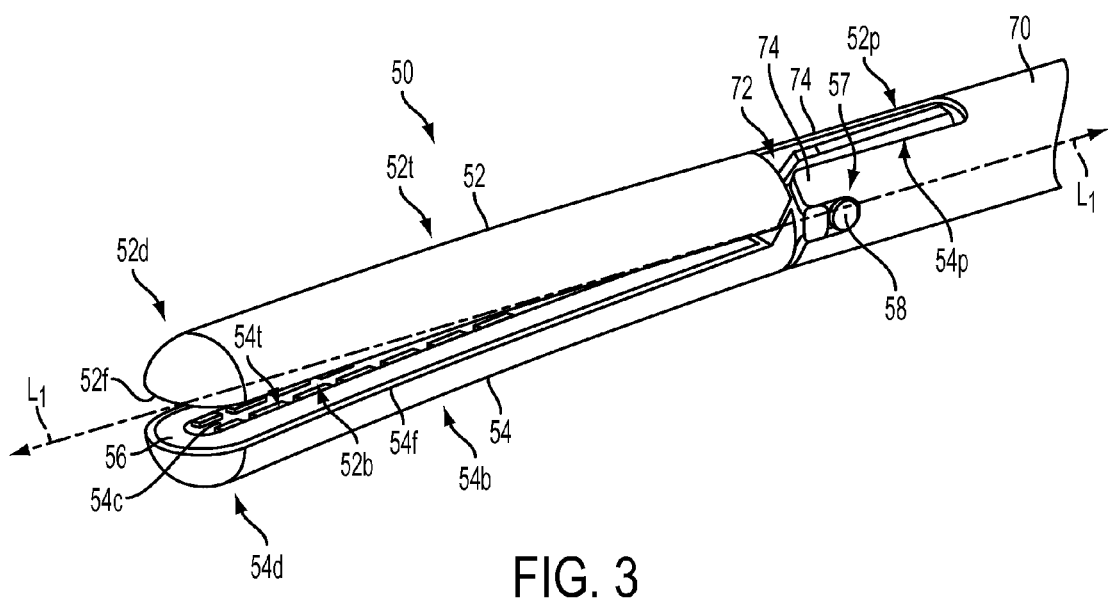
FIG. 3 is a perspective view of the end effector of FIG. 2, the first and second jaws being in a generally closed position.
Figure 4:
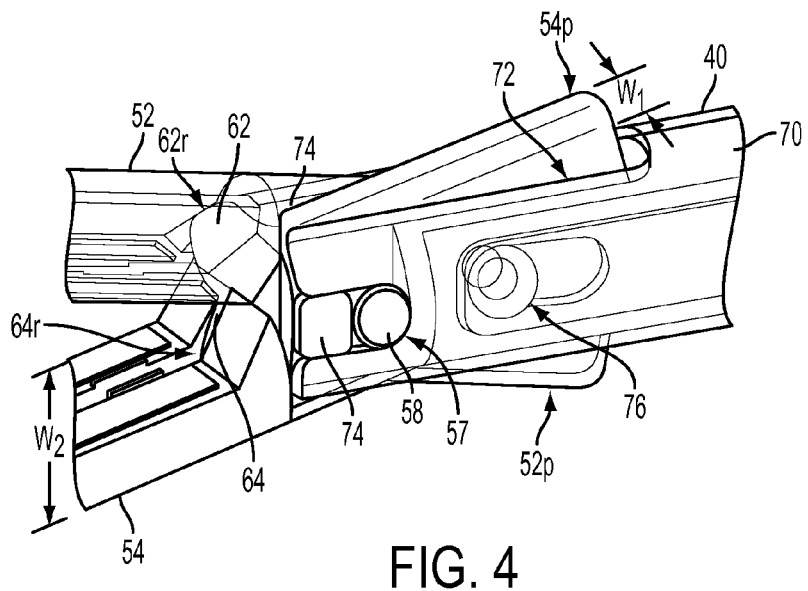
FIG. 4 is a partially transparent, detailed perspective view of the end effector and shaft of FIG. 2, illustrating an approximate location at which the first and second jaws pivot with respect to each other.

The end effector 50 can have a variety of sizes, shapes, and configurations. As shown in FIGS. 2-4, the end effector 50 is a clamp having upper and lower jaws 52, 54 that are pivotally connected to each other so they can rotate with respect to each other to grasp tissue therebetween. As shown best in FIG. 4, proximal ends 52p, 54p have a width $w_1$ that is smaller than a width $w_2$ of the remaining portion of the respective jaws 52, 54 so that the proximal portions 52p, 54p can be disposed within a slot 72 formed by arms 74 at a distal end of the pusher 70. The pivotal connection of the jaws 52, 54 can be located at a pivot point 57 at which a pin 58 is disposed through the arms 74 and through a portion of the upper and lower jaws 52, 54. Such a configuration allows the upper and lower jaws 52, 54 to pivot with respect to each other, with the proximal ends 52p, 54p rotating within the slot 72 as the jaws 52, 54 are moved between an open position or configuration, illustrated in FIG. 2, and a closed position or configuration, illustrated in FIG. 3 as a generally closed position. Although the jaws 52, 54 in FIG. 3 are not fully clamped together, the illustrated configuration can still be considered a closed configuration in instances in which tissue disposed therebetween is so thick that it prevents the jaws 52, 54 from being fully clamped together. In other embodiments, the tissue can be thinner, thereby allowing the jaws 52, 54 to be disposed more proximate to each other, or even fully clamped together, in the closed position.

In the open configuration, a portion of the proximal ends 52p, 54p can extend outside of the slot 72, while in the closed configuration the proximal ends 52p, 54p can sit substantially within the slot 72 such that proximal ends 52p, 54p do not extend outside of the slot 72. A person skilled in the art will understand that the location and configuration of the proximal ends 52p, 54p with respect to the pusher 70 and the shaft 40 can change, depending at least in part on the size and shape of the jaws 52, 54, the shaft 40, the pusher 70, and components with which they are used. Still further, in other embodiments, one of the jaws 52, 54 can pivot towards the other while the other remains substantially stationary. In use, the upper jaw 52 can be configured to operate as an anvil to deploy staples of a staple cartridge associated with the lower jaw 54. In the present disclosure, the upper jaw 52 may sometimes be referred to as a first jaw or anvil, and the lower jaw 54 may sometimes be referred to as a second jaw or staple cartridge receiver.

Each of the upper and lower jaws 52, 54 can be generally elongate in shape. A top surface 52t of the upper jaw 52 can be rounded, while a bottom, tissue-engaging surface 52b, sometimes referred to herein as a face 52f, can be configured to grasp tissue. As shown, the bottom surface 52b is substantially flat, although in some embodiments the surface can include a plurality of teeth or other surface features to assist in gripping tissue disposed between the jaws 52, 54 by increasing the friction therebetween. Likewise, a bottom surface 54b of the lower jaw 54 can be rounded, while a top, tissue-engaging surface 54t, which is adjacent and opposed to the bottom surface 52b of the upper jaw 52, can be configured to grasp tissue. The top, tissue-engaging surface 54t is sometimes referred to herein as a face 54f. As shown, the top surface 54t is substantially flat, although in some embodiments the surface can include a plurality of grooves that are complementary to teeth formed on the bottom surface 52b to assist in gripping tissue disposed between the jaws 52, 54.

In embodiments in which the surgical device is further configured to seal the tissue, one or more components useful for sealing tissue disposed between the jaws can be included as part of the end effector. In the illustrated embodiment, an electrode 56 is associated with the top surface 54t of the lower jaw 54 using any manner known to those skilled in the art, including, by way of non-limiting example, using an adhesive. In some exemplary embodiments, the electrode 56 can made from a positive temperature coefficient (PTC) polymer or matrix that provides homogeneous and precisely regulated energy delivery with low thermal spread. The PTC conductive-resistive matrix can be a variably resistive body that comprises a polypropylene or a medical grade silicone polymer that is doped with conductive particles (e.g., carbon). Polymer PTC materials are known in the field of over current protection devices that will "trip" and become resistant when a selected trip current is exceeded. Although in the illustrated embodiment the electrode 56 is a single electrode that is associated with the lower jaw 54, in other embodiments multiple electrodes can be used, and one or more electrodes can be disposed on either or both of the upper and lower jaws 52, 54.

A person skilled in the art will appreciate that the first and second jaws 52, 54 can have any suitable shape and length for engaging tissue, with the shape, length, and overall configuration being selected, at least in part, based on the targeted anatomical structure for treatment and the other components with which the jaws 52, 54 are being used. As shown best in FIG. 3, each of the jaws is curved laterally with respect to the longitudinal axis $L_1$ of the shaft 40. Thus, while a midpoint of the proximal end 52p, 54p of the first and second jaws 52, 54 is disposed substantially along the longitudinal axis $L_1$, a midpoint of the distal end 52d, 54d of the first and second jaws 52, 54 is disposed a distance away from the longitudinal axis $L_1$. Such a configuration can allow the end effector 50 to more easily fit a curved organ against a concave portion of the curve formed in the jaws 52, 54. In other embodiments, the jaws 52, 54 can be substantially straight such that the midpoints of the proximal ends 52p, 54p and the midpoints of the distal ends 52d, 54d are both disposed substantially along the longitudinal axis $L_1$.

As shown in FIG. 2, each jaw 52, 54 can include a centrally disposed track or axial channel 52c, 54c formed therein, with the two tracks 52c, 54c being complementary of each other such that together they form a single track for the end effector 50. The tracks 52c, 54c can be centrally disposed with respect to a width of each jaw 52, 54. Further, the tracks 52c, 54c can be configured to receive a cutting mechanism 60, as described further below.

In the illustrated embodiment the tracks 52c, 54c are formed in the opposed faces 52f, 54f of the jaws 52, 54, and extend through a portion of the jaws 52, 54 towards their respective top and bottom surfaces 52t, 54b. Each track 52c, 54c can be generally elongate having a length that extends a substantial portion of a length of the jaws 52, 54, a width that is wider than a total thickness of the cutting mechanism 60 configured to be disposed therein, and a depth that is deep enough to receive the cutting mechanism 60 disposed therein but terminates prior to a terminal end surface of the respective top and bottom portions 52t, 54b. The tracks 52c, 54c in the illustrated embodiment have a curved shape that mimics the curve of the jaws 52, 54, although a variety of other shapes can also be formed therein that allow for a cutting mechanism to travel therethrough. The shape, length, width, and depth of the tracks 52c, 54c can depend on a variety of different factors, including, by way of non-limiting example, the dimensions of the cutting mechanism and jaws and the type of procedure with which the device will be used. A person skilled in the art will recognize any number of track configurations that can be used in conjunction with the disclosures provided for herein. For example, in some embodiments, the depths of the tracks 52c, 54c can be such that the tracks 52c, 54c extend through the respective top and bottom surfaces 52t, 54b. In the illustrated embodiment, the depths of the tracks 52c, 54c terminate at respective bases 52cb, 54cb of the tracks 52c, 54c.

Other features can be incorporated into the end effector 50. By way of non-limiting example, features for measuring or otherwise determining an amount of force and/or compression applied to the tissue by the jaws 52, 54 can be incorporated into the device 10. Likewise, components configured to notify an operator when certain threshold values, e.g., loads, are attained can be provided, whether such notification is visual, audible, or in some other form. A person skilled in the art will understand exemplary components having these features and will also understand how to integrate such components with the present disclosures. Additionally, any type of material known to those skilled in the art can be used to manufacture the components of the end effector 50, the shaft 40, and the handle portion 20. In some exemplar embodiments, the jaws 52, 54 and shaft 40 are made from surgical grade stainless steel (e.g., 17-4), the housing 22 of the handle portion is made from a polymer (e.g., polycarbonate), and components disposed in the handle portion, e.g., motors, controllers, levers, are made from various materials typically used to form such components.

Cutting Mechanism—Two Cutting Blades

Figure 5:
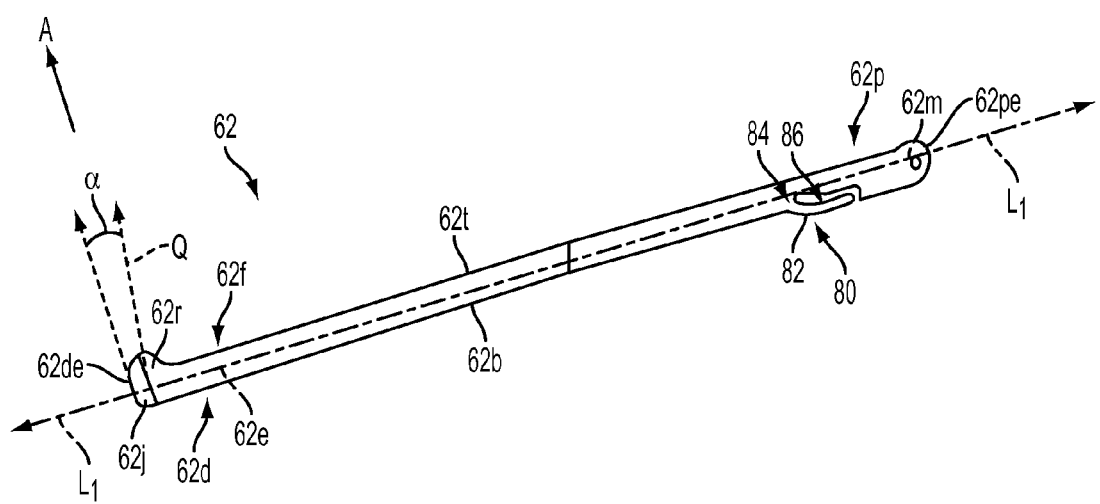
FIG. 5 is a perspective view of the first cutting blade of FIG. 2.
Figure 6:
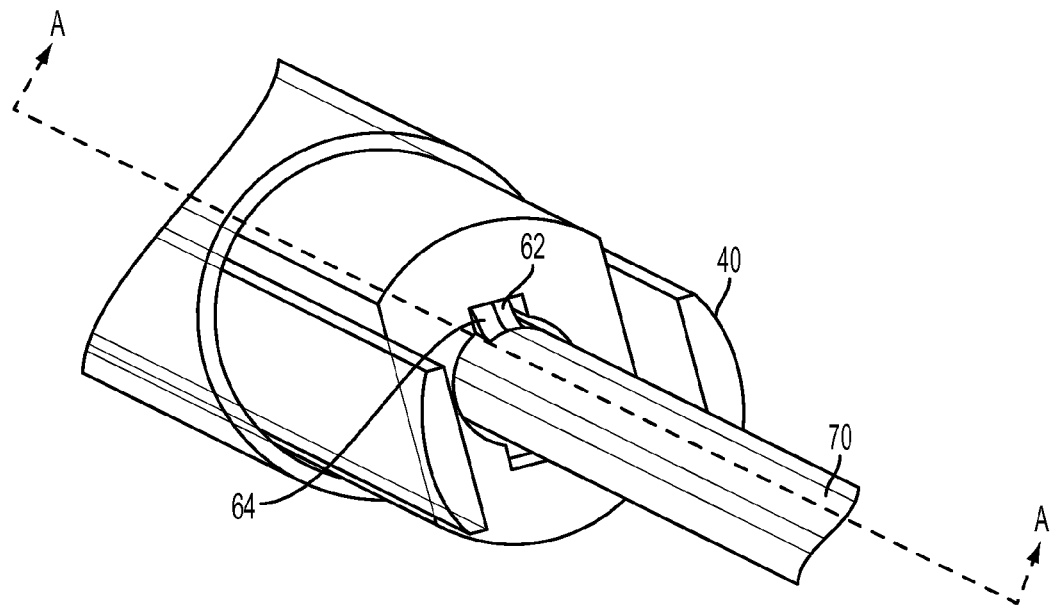
FIG. 6 is a partially transparent perspective view of proximal ends of the first and second cutting blades being coupled to an actuation rod of the surgical device of FIG. 2.

The tracks 52c, 54c of the jaws 52, 54 can be configured to receive a cutting mechanism 60. In the embodiment illustrated in FIGS. 2 and 4, the tracks 52c, 54c are configured to receive two elongate cutting blades 62, 64. The two elongate cutting blades 62, 64 of the illustrated embodiment are structurally the same, but they are disposed in the end effector 50 such that a rounded distal tip 62r of one cutting blade 62 faces the base 52cb of the track 52c and a rounded distal tip 64r of the other cutting blade 64 faces the base 54cb of the track 54c. FIG. 5 illustrates one exemplary embodiment of one cutting blade 62 of the cutting blades 62, 64.

Figure 8A:
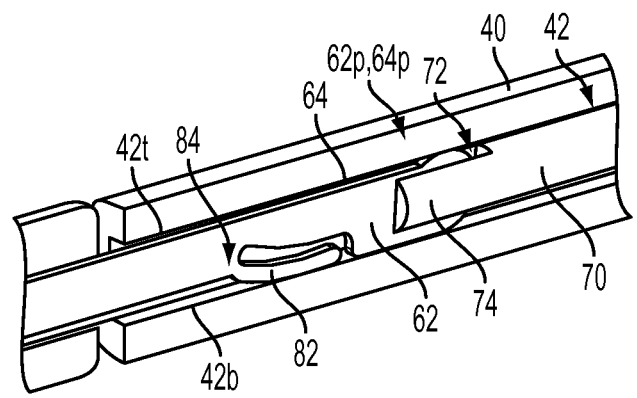
FIG. 8A is a perspective cross-sectional view of the surgical device, blades, and actuation rod of FIG. 6 taken along the line A-A.
Figure 9:
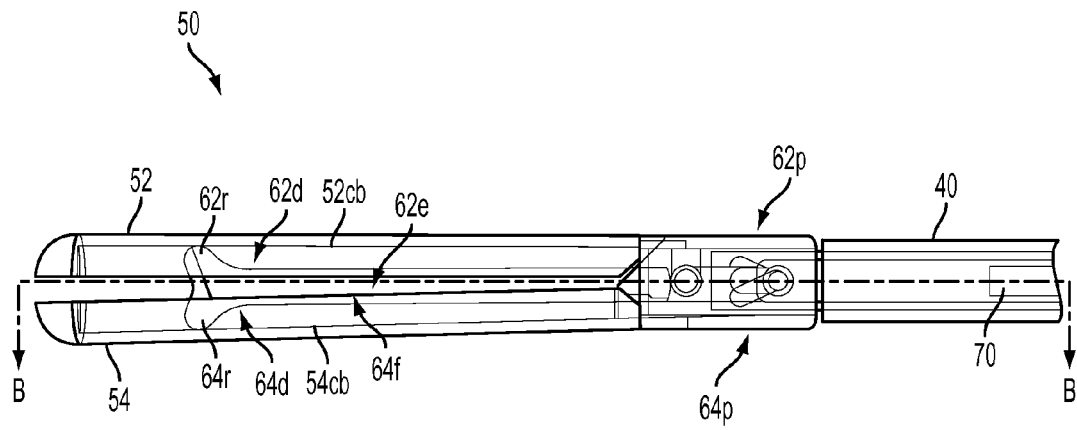
FIG. 9 is a partially transparent side view of the first and second jaws and first and second cutting blades of FIG. 2.
Figure 10:
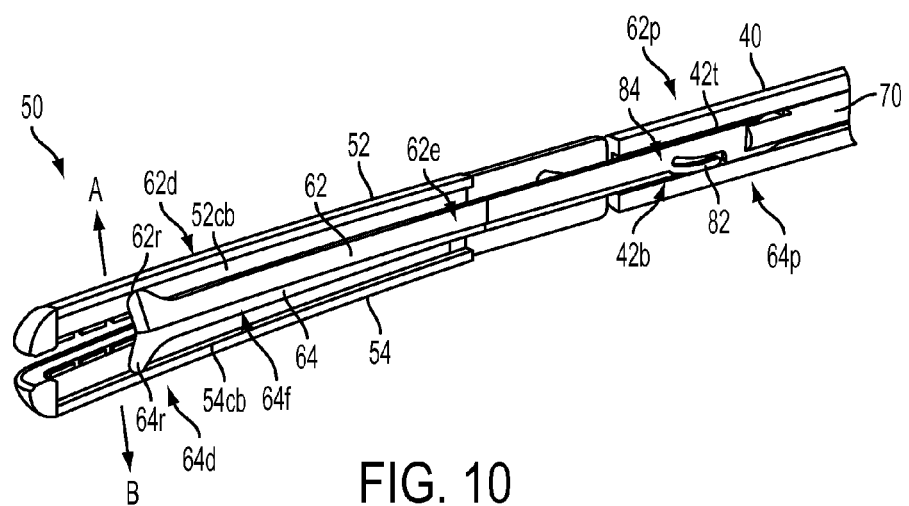
FIG. 10 is a perspective cross-sectional view of the jaws and cutting blades of FIG. 9 taken along the line B-B.
Figure 11:
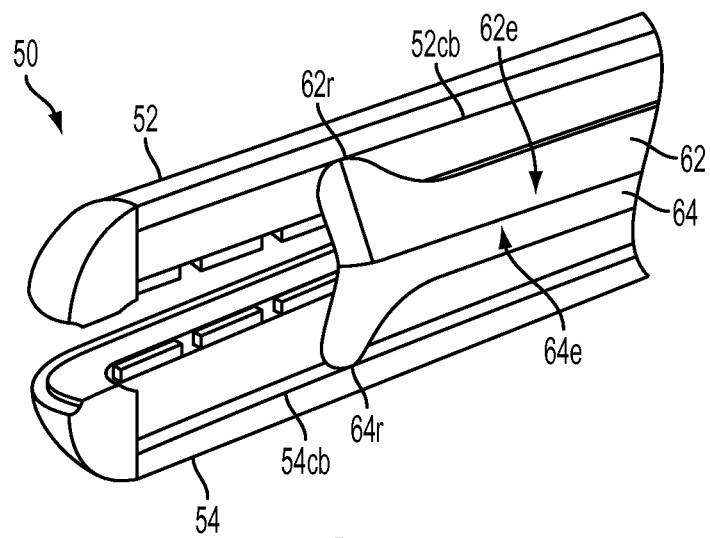
FIG. 11 is a perspective, detailed cross-sectional view of the jaws and cutting blades of FIG. 10.

The cutting blade 62 is defined by a proximal end 62pe, a distal end 62de, a top surface 62t, a bottom surface 62b, and opposed side surfaces 62e, 62f, the opposed side surfaces 62e, 62f forming a substantial portion of a surface area of the cutting blade 62. A proximal portion 62p of the cutting blade 62 can be configured to couple to an actuation rod 70 associated with the handle assembly, as shown at least in FIGS. 6-8B in which the two cutting blades 62, 64 are coupled to the actuation rod 70. Further, a distal portion 62d of the cutting blade 62 can be configured to cut tissue disposed between jaws with which the blade 62 is associated when the blade is advanced distally, i.e., axially, as shown in FIGS. 9-11. The resulting configuration illustrated in FIGS. 9-11 is one in which together the two blades 62, 64 form a single cutting surface. The proximal portion 62p can also include a biasing element, as shown a spring mechanism 80, configured to bias the rounded distal tip 62r of the cutting blade 60 in an upward direction A.

The proximal portion 62p can have any configuration that allows the cutting blade 62 to be coupled to an actuation rod that is controlled by the handle assembly. As shown, the proximal portion 62p includes a lumen 62m formed therein for receiving a pin 66 (FIG. 8B). The pin 66 can be disposed through each blade 62, 64 of the cutting mechanism and can be coupled to a portion of the actuation rod 70 to secure the location of the pin 66 with respect to the cutting mechanism 60. In the illustrated embodiment the pin 66 is received by bores 76 (FIG. 4) formed in opposed first and second arms 74 of the actuation rod 70. As shown, the pin 66 is not configured to be disposed all the way through either of the two arms 74, although in other embodiments the pin 66 can extend through one or both arms 74. The resulting configuration of the actuation rod 70 and the cutting blades 62, 64 is such that distal advancement and proximal retraction of the actuation rod 70 via the handle assembly also causes respective distal advancement and proximal retraction of the cutting blades 62, 64. Any other technique known to those skilled in the art for associating a cutting blade with an actuator can also be used to allow manipulation of the handle assembly to control movement of the cutting blades 62, 64.

The spring mechanism 80, which is also formed in the proximal portion 62p of the cutting blade 62, is configured to help bias the rounded distal tip 62r in the direction A. As shown, the spring mechanism 80 is formed proximate to the bottom surface 62b of the cutting blade 62. The spring mechanism 80 can include an elongate, curved flexing arm 82 that is configured to flex or rotate about a pivot point 84 of the spring mechanism 80. As shown, the pivot point 84 can be distal of the elongate flexing arm 82, although in other embodiments the pivot point 84 can be proximal of the elongate flexing arm 82 such that the elongate flexing arm 82 extends distally away from the pivot point 84. An elongate cut-out 86 can be formed in a portion of the cutting blade 62, extending through the opposed side surfaces 62e, 62f to form the elongate flexing arm 82. As shown in FIG. 8A, when disposed in the surgical device, the elongate flexing arm 82 can be disposed against a bottom surface 42b of the lumen 42 formed in the shaft 40 that receives the actuation rod 70 and the cutting mechanism 60. The biasing interaction between the arm 82 and the bottom surface 42b can cause the cutting blade 62 to be biased in the upward direction A, which as shown in FIG. 10 is towards the base 52cb of the track 52c of the upper jaw 52. More particularly, the rounded distal tip 62r can be biased in a plane that is substantially co-planar with the page.

Figure 7:
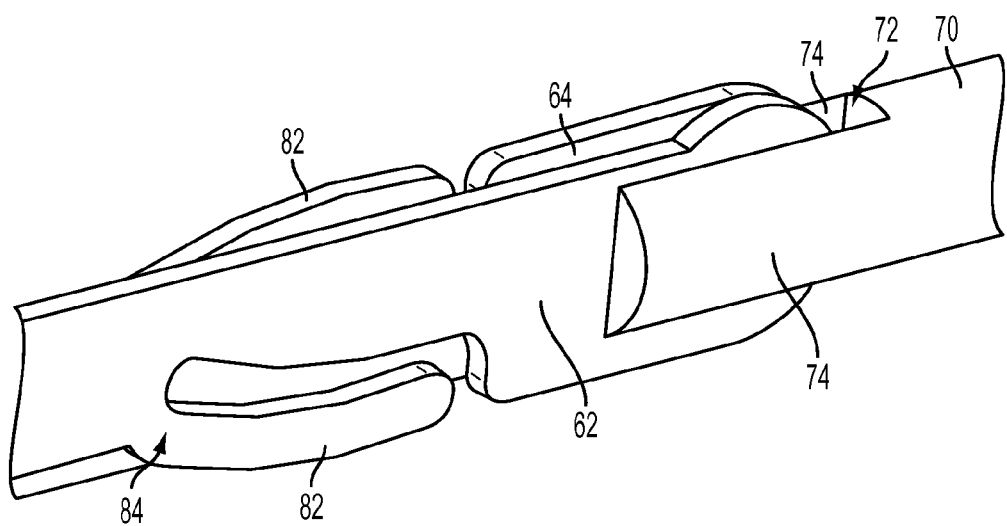
FIG. 7 is a perspective view of the first and second cutting blades and actuation rod of FIG. 6.
Figure 8B:
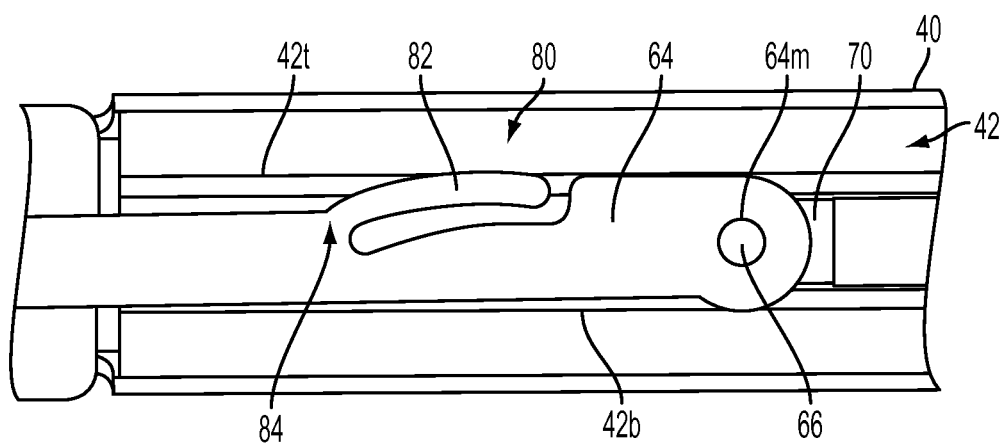
FIG. 8B is a side cross-sectional view of the surgical device, blades, and actuation rod of FIG. 8A, with the first cutting blade and one arm of the actuation rod being hidden from view.

The second cutting blade 64 can have an identical configuration as the blade 62, but as shown in FIGS. 7 and 8B it is flipped 180 degrees such that a second side surface 64f of the second cutting blade 64 is adjacent and opposed to the second side surface 62f of the first cutting blade 62. Generally, the first cutting blade 62 is in contact with the second cutting blade 64 so that tissue is less likely to get caught between the two blades. As shown in FIG. 8B, the orientation of the second cutting blade 64 when it is disposed in the surgical device can be such that its elongate flexing arm 82 can be disposed against an opposed top surface 42t of the lumen 42 of the shaft 40. The biasing interaction between the arm 82 and the top surface 42t can cause the cutting blade 64 to be biased in a downward direction B, which as shown in FIG. 10 is towards the base 54cb of the track 54c of the lower jaw 54. More particularly, the rounded distal tip 64r of the cutting blade 64 can be biased in the same plane as the rounded distal tip 62r is biased, but in the opposite direction.

The distal portion 62f of the cutting blade 62 can include a cutting edge 62j formed at its terminal, distal end 62de. As shown, the cutting edge 62j is disposed in a substantially vertical direction, forming a small angle α between a straight axis Q that extends perpendicular to the longitudinal axis $L_1$. The angle α can be approximately in the range of about 0 degrees to about 25 degrees. The cutting edge 62j is sharp such that it can transect or otherwise cut tissue it passes through. In the illustrated embodiment, the cutting edge 62j extends the entire vertical length of the cutting blade 62, although in other embodiments the cutting edge 62j can extend less than the entire vertical length of the cutting blade 62.

As shown, the top portion 62r of the cutting blade 62 disposed at the distal portion 62d can have a rounded configuration to allow it to easily translate through the track 52c as it is advanced therethrough. Accordingly, in instances in which the rounded distal tip 62r is biased into engagement with the base 52cb of the track 52c, it can slide along the track 52c without difficulty. The distal portion 62d, however, can have a variety of other configurations designed for cutting tissue and traveling through jaws of an end effector without departing from the spirit of the present disclosure.

As shown in FIGS. 9-11, the cutting edges 62j, 64j of the first and second cutting blades 62, 64 can be configured to operate together such that they can act as a single cutting surface. As a result, in embodiments in which the rounded distal tips 62r, 64r are configured to engage the respective surfaces 52cb, 54cb of the tracks 52c, 54c, the single cutting surface can extend an approximate entire vertical length between the bases 52cb, 54cb. In the illustrated embodiment, because the cutting edges 62j, 64j extend at a non-perpendicular angle with respect to the longitudinal axis $L_1$, the single cutting surface has a V shape with the apex of the V being more proximal than the ends of the V. In some embodiments, the rounded distal tips 62r, 64r can actually be coupled together, sometimes referred to as being laminately restrained, for instance by a physical structures such as a pin or rivet disposed therebetween or a band or clip attached thereto to hold the two blades 62, 64 together. Alternatively, laminate restraint can be provided by treating the surfaces of the distal tips 62r, 64r. For example, the surfaces that come into contact with each other to be hooked together can be highly polished, which can provide a surface tension resulting from the finish sufficient to maintain the location of the distal tips 62r, 64r with respect to each other. Providing for a laminate restraint can help minimize any tissue becoming caught between the first and second cutting blades. Generally, as the cutting blades 62, 64 distally advance through jaws 52, 54, they can shift with respect to each other such that one blade extends a bit further distally than the other. As shown in FIGS. 9-11, the cutting blade 64 advances a little further distally than the cutting blade 62. The coupling of the two blades 62, 64 can generally be of the nature that the two blades 62, 64 are not completely fixed with respect to each other, thus allowing for the two blades 62, 64 to shift slightly lengthwise with respect to each other as shown. Further, as also shown in FIGS. 9-11, as the distance between the faces 52f, 54f of the jaws 52, 54 increases in the distal direction, the cutting blades 62, 64 begin to extend away from each other because they are biased towards their respective jaws 52, 54. Thus, more of the surface area of the side surfaces 62e, 62f and 64e, 64f become visible as the blades 62, 64 advance distally in the illustrated embodiment. In embodiments in which the device is being used to cut thick tissue, the faces 52f, 54f of the jaws 52, 54 can be particularly far apart. Thus, the biasing of the blades 62, 64 towards the bases 52cb, 54cb is particularly helpful in maintaining a location of the blades 62, 64 within the tracks 52c, 54c.

In alternative embodiments, the distal ends 62de, 64de of the two blades 62, 64 can be hooked or locked together without using a separate coupling element such as a pin. For example, the second side surface 62f of the first cutting blade 62 can be deflected around the second cutting blade 64 such that the surface 62f is adjacent to the second side surface 64f of the second blade 64. Configurations of this nature are discussed in more detail below with respect to FIGS. 20-27. Further, a person skilled in the art will recognize that any number of techniques disclosed herein or otherwise known to those skilled in the art can be used to help maintain a location of the first distal tip 62r with respect to the second distal tip 64r, thereby maintaining a single cutting surface. The coupling of the distal tips 62r, 64r, however, can be flexible enough to allow the distal tips 62r, 64r to move towards and away from each other as the cutting blades 62, 64 advance distally and retract proximally, for instance to accommodate varying tissue thickness.

The cutting blades 62, 64 provided for herein can have a variety of shapes and configurations, depending, at least in part, on the shapes, sizes, and configurations of the other components with which the blades are being used and the type of procedure in which the cutting blades are being used. For example, in some exemplary embodiments a length of a cutting blade used in conjunction with a tissue cutting device having a shaft with a 5 millimeter diameter can be about 45 millimeters while a length of a cutting blade used in conjunction with a tissue cutting device having a shaft with a 10 millimeter diameter can be about 70 millimeters. More generally, a length of the cutting blade can be in the range of about 30 millimeters to about 100 millimeters and a width, i.e., the vertical length, of the cutting blade can be in the range of about 3 millimeters to about 10 millimeters, also depending on the size of the shaft in which it is to be disposed.

Generally, a thickness of the cutting blade can be thin to allow the blade to flex and go around curved tracks in which they are disposed. In some exemplary embodiments, a thickness of the blade can be in the range of about 0.1 millimeters to about 0.5 millimeters, and in one embodiment the thickness is in the range of about 0.2 millimeters. Further, the cutting blades can be formed from a variety of materials known to those skilled in the art. Generally, the material(s) used to form the cutting blade can be flexible to allow the blade to easily bend through a curved track. For example, a metal such as a surgical grade stainless steel (e.g., 17-4) or Nitinol can be used to form the cutting blades.

In use, the spring mechanisms 80 on the first and second cutting blades 62, 64 allows the vertical height of the single cutting surface formed by the distal tip portions 62r, 64r to be greater than a distance between the tissue-engaging surfaces 52f, 54f of the first and second jaws 52, 54 at equivalent axial locations as the cutting blades 62, 64 translate axially through a portion of the first and second jaws 62, 64. As shown in FIGS. 2 and 4, the device begins in an open configuration in which the jaws 52, 54 are open and the rounded distal tips 62r, 64r are at a proximal location, adjacent to the pivot point 57. After the tissue or blood vessel to be transected and/or sealed is disposed in the jaws 52, 54, the handle assembly can be manipulated to move the jaws 52, 54 to the closed configuration, as shown in FIG. 3, in which tissue is engaged by the tissue-engaging surfaces 52f, 54f, thereby clamping the tissue. After the jaws 52, 54 are initially closed, the cutting blades 62, 64 can remain at their proximal location. In embodiments in which the tissue or vessel is being sealed prior to being cut, the cutting blades 62, 64 can typically remain proximate to the proximal location so that cutting is not performed until after the sealing has at least started, or typically until it is completed. The tissue can be sealed by energy supplied though the electrode 56, the electrode 56 being operated by one or more features incorporated into the handle assembly to activate the electrode.

As shown in FIGS. 9-11, after the tissue is sealed, a cutting stroke can be performed by distally advancing the cutting blades 62, 64 through at least a portion of the jaws 52, 54 to cut the tissue disposed between the jaws 52, 54. In embodiments in which the device 10 is not configured to seal tissue, the blades 62, 64 can be advanced distally any time after the jaws 52, 54 are closed. In some embodiments the blades 62, 64 can be configured to help cam the jaws 52, 54 closed, and thus the blades 62, 64 can also be configured to advance while the jaws 52, 54 are being closed. While configurations in which a cutting mechanism is used to also close a jaw assembly are known to those skilled in the art, some non-limiting exemplary embodiments of such a configuration are provided for in U.S. patent application Ser. No. 14/149,279 entitled "Electrosurgical Sealing and Transecting Devices and Methods with Improved Application of Compressive Force," which was filed on Jan. 7, 2014, the content of which is incorporated by reference herein in its entirety.

As the cutting blades 62, 64 move from their proximal location to their more distal location, which is illustrated in FIGS. 9-11, the flexing arms 82 can remain in contact with the surfaces 42b, 42t of the lumen 42 of the shaft 40, thereby continuing to bias the cutting blades 62, 64 into the respective tracks 52c, 54c of the upper and lower jaws 52, 54. In the illustrated embodiment, the rounded distal tips 62r, 64r can remain in contact with the respective bases 52cb, 54cb of the tracks 52c, 54c during a substantial entirety of the cutting stroke. The biasing force applied to the blades 62, 64 allows them to be self-adjusting as they translate through the jaws 52, 54, which in turn makes it difficult for the blades 62, 64 to be displaced from or otherwise fall out of the tracks 52c, 54c. In other embodiments, the rounded distal tips 62r, 64r may extend into the tracks 52c, 54c but may not reach their respective bases 52cb, 54cb. Such embodiments can still be effective to allow the cutting blades 62, 64 to cut tissue and be self-adjusting to remain disposed in their respective tracks 52c, 54c of the end effector 50 during use.

Figure 12:
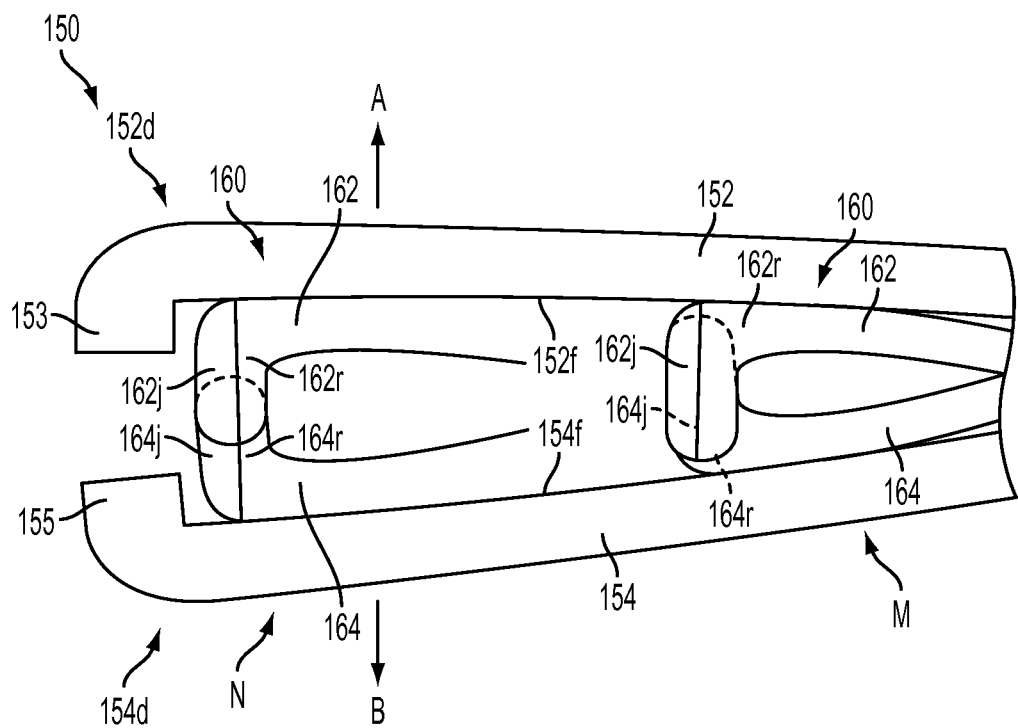
FIG. 12 is a schematic, progressive side view of another exemplary embodiment of an end effector of a surgical device in which distal ends of first and second cutting blades are advanced progressively from a proximal location to a more distal location with respect to the end effector.

FIG. 12 illustrates an alternative embodiment of an end effector 150 having a cutting mechanism 160 that includes two cutting blades 162, 164. The end effector 150 can include opposed first and second jaws 152, 154 that are pivotally connected to each other to move between an open position and a closed position. In the illustrated embodiment, the jaws 152, 154 are disposed approximately in the closed position. Each of the distal ends 152d, 154d of the jaws 152, 154 can include a retention tab 153, 155 that is configured to prevent the cutting blades 162, 164 disposed therein from advancing distally beyond the jaws 152, 154. As shown, tissue-engaging surfaces 152f, 154f of the first and second jaws 152, 154 can be tapered such that a distance between the two surfaces 152f, 154f increases in the distal direction when the jaws 152, 154 are in the closed position. Alternatively, as described with respect to FIG. 3, the tapered configuration between faces 152f and 154f can result from a thickness of tissue.

In the illustrated embodiment, the jaws 152, 154 do not include grooved tracks along through which the cutting blades 162, 164 can travel. Instead the cutting blades 162, 164 can travel along the tissue-engaging surfaces 152f, 154f of the jaws. In alternative embodiments, a small groove, or a more defined track similar to the tracks 52c, 54c described above for the end effector 50 can be formed in the jaws 152, 154 and used in conjunction with the cutting blades 162, 164.

The cutting blades 162, 164 can generally be of a nature similar to the cutting blades 62, 64 in that they include cutting edges 162j, 164j that extend the approximate vertical length of the cutting blades 162, 164, and the blades 162, 164 are biased in the respective directions A and B, which is a direction towards the surfaces 152f, 154f along which they are configured to travel. As shown, distal tips 162r, 164r extend in a direction opposite to the direction of the cutting blades 62, 64 of the cutting mechanism 60 of FIGS. 9-11. Thus, although the first, top cutting blade 162 is biased in the upward direction A, towards the first jaw 152, the distal tip 162r faces towards the second jaw 154, and thus it extends in the downward direction B. Likewise, although the second, bottom cutting blade 164 is biased in the downward direction B, towards the second jaw 154, the distal tip 164r faces towards the first jaw 152, and thus it extends in the upward direction A.

Any number of techniques can be used to bias the cutting blades 162, 164 in their respective directions A and B, including but not limited to the techniques described herein or otherwise known to those skilled in the art. As shown in FIG. 12, as the cutting blades 162, 164 are advanced from a more proximal position, identified as position M, to a more distal position, identified as position N, the cutting blades 162, 164 remain biased in their respective directions A and B, but an amount of overlap between the distal tips 162r, 164r decreases because the tissue-engaging surfaces 152f, 154f are tapered. Nevertheless, as shown, even in the more distal position N, the distal tips 162r, 164r still overlap to form a single cutting surface that remains biased against the jaws 152, 154, thereby preventing the cutting blades 162, 164 from becoming dislodged or otherwise disassociated from the jaws 152, 154. Further, in some embodiments, the distal tips 162r, 164r can be coupled to each other using any number of techniques disclosed herein or otherwise known to those skilled in the art to help maintain the single cutting surface formed by the two cutting edges 162j, 164j while still allowing some movement of the tips 162r, 164r along the plane of the page as the tips 162r, 164r advance distally and retract proximally.

Figure 13:
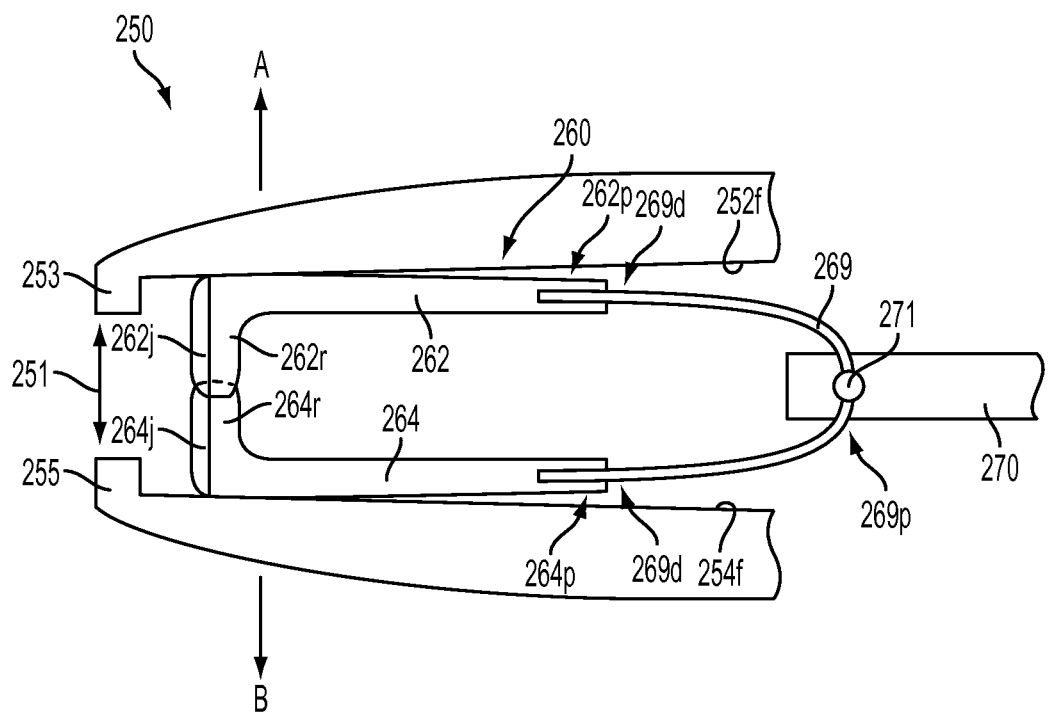
FIG. 13 is a schematic side view of still another exemplary embodiment of an end effector of a surgical device in which first and second cutting blades are coupled to an actuation rod by a biasing element.

FIG. 13 illustrates another alternative embodiment of an end effector 250 having a cutting mechanism 260 that includes two cutting blades 262, 264. Similar to the end effector 150 of FIG. 12, the end effector 250 includes opposed first and second jaws 252, 254 that are pivotally connected to each other such that the jaws 252, 254 can move between an open and a closed position, as illustrated by the arrows 251. In the illustrated embodiment, the jaws 252, 254 are disposed approximately in the closed position, and each of the distal ends 252d, 254d of the jaws 252, 254 includes a retention tab 253, 255. The tissue-engaging surfaces 252f, 254f of the jaws 252, 254 in this embodiment are not shown as being tapered, although they can be tapered. As shown, the cutting blades 262, 264 can travel along the tissue-engaging surfaces 252f, 254f. In alternative embodiments, a groove or track can be formed in one or both of the jaws 252, 254 to help guide a travel path for the cutting blades 262, 264.

The cutting blades 262, 264 are configured similar to the cutting blades 162, 164 of FIG. 12, and thus include cutting edges 262j, 264j that extend the approximate vertical length of the cutting blades 262, 264, distal tips 262r, 264r that extend towards the jaws 252, 254 that the blade 262, 264 is not biased towards, and the blades 262, 264 are generally configured to be biased towards the faces 252f, 254f of the jaws 252, 254 along which they are configured to travel. Although a variety of biasing techniques can be used to bias the blades 262, 264 towards their respective jaw faces 252f, 254f, in the illustrated embodiment proximal ends 262p, 264p of the blades 262, 264 are coupled to distal ends 269d of a leaf spring 269 that biases the first cutting blade 262 in the upward direction A and the second cutting blade 264 in the downward direction B. As shown, a proximal end 269p of the leaf spring 269 can be fixedly coupled to an actuation rod 270, for instance by a spot weld 271, such that as the actuation rod 270 is advanced distally and retracted proximally by the handle assembly, the leaf spring 269 and blades 262, 264 associated therewith are also advanced distally and retracted proximally. As shown, the distal tip portions 262r, 264r can overlap with each other to form a single cutting surface, and the distal tips 262r, 264r can be coupled to each other in a flexible manner using techniques described elsewhere herein.

Figure 14:
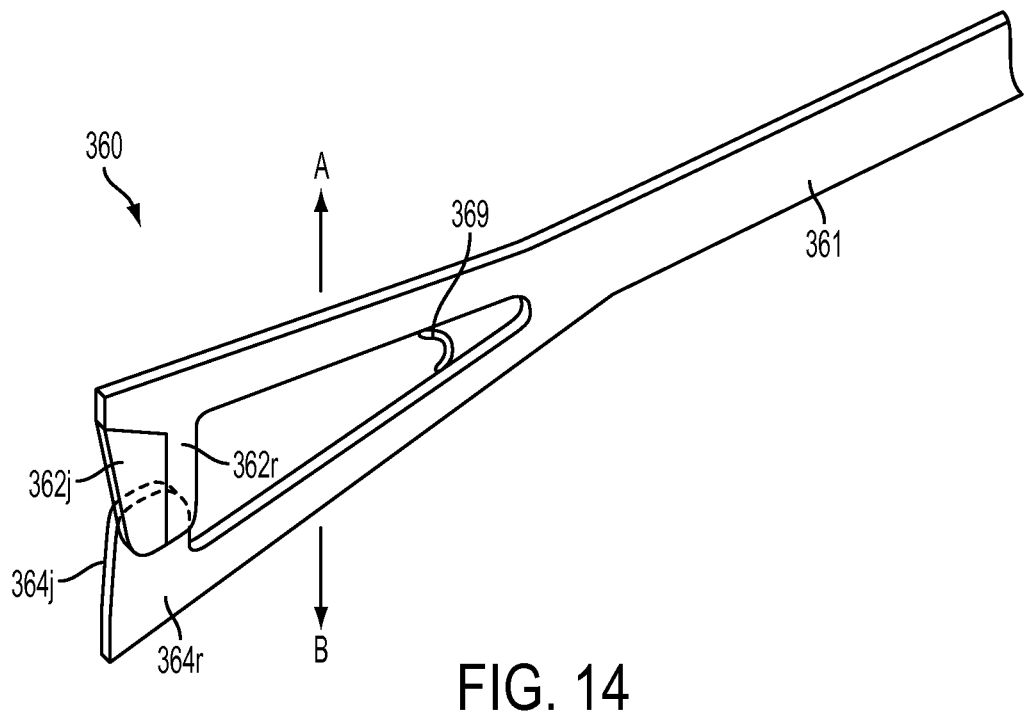
FIG. 14 is a perspective view of one exemplary embodiment of a cutting mechanism having first and second cutting blades.

FIG. 14 illustrates an alternative embodiment of a cutting mechanism 360 for use in conjunction with any of the end effectors disclosed herein or otherwise known to those skilled in the art. As shown, the cutting mechanism 360 is a single, unitary structure having a proximal shaft 361 and two opposed cutting blades 362, 364 extending therefrom. The cutting blades 362, 364 are similar to the cutting blades 162, 164 and 262, 264 of FIGS. 12 and 13 in that they include cutting edges 362j, 364j that extend the approximate vertical length of the respective cutting blades 362, 364 and they include distal tips 362r, 364r that extend towards a jaw that the blade 362, 364 is not biased towards. A biasing element, such as a leaf spring 369, can be disposed between the two blades 362, 364 to bias the first blade 362 in the direction A and the second blade 364 in the direction B. The two distal tips 362r, 364r can overlap with each other to form a single cutting surface. The distal tips 362r, 364r can be coupled to each other to help maintain the single cutting surface as described elsewhere herein.

Figure 15A:
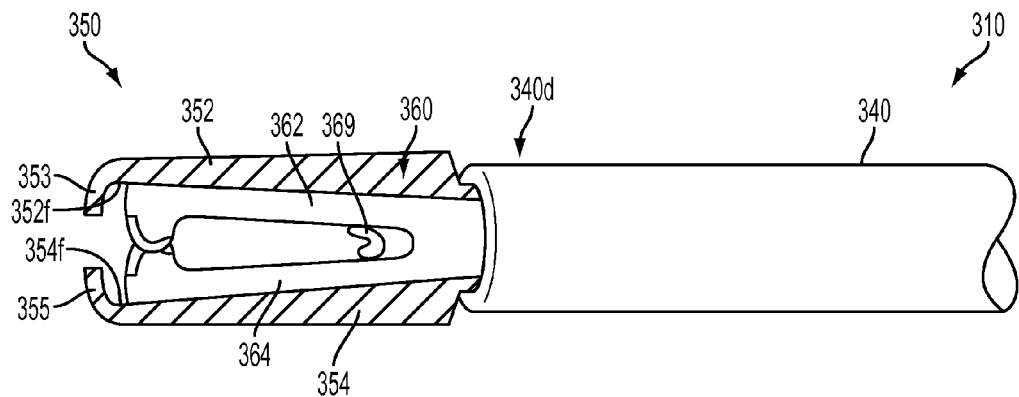
FIG. 15A is a side perspective view of the cutting mechanism of FIG. 14 being disposed in first and second jaws of a surgical device, the first and second jaws being in an open position.
Figure 15B:
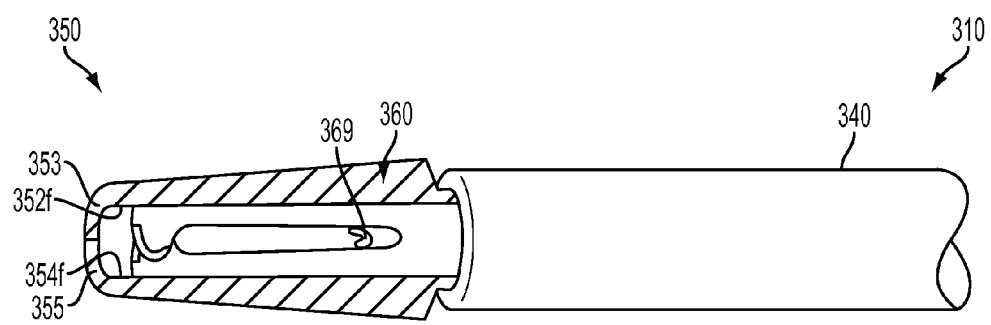
FIG. 15B is a side perspective view of the cutting mechanism of FIG. 15A, the first and second jaws being in a closed position.

FIGS. 15A and 15B illustrate the cutting mechanism 360 in use in conjunction with an end effector 350. As shown, a pair of opposed jaws 352, 354 similar to the jaws 152, 154 and 252, 254 of FIGS. 12 and 13 are associated with a shaft 340 of a surgical device 310. The proximal shaft 361 and proximal ends of the jaws 352, 354 can be disposed within a distal portion 340d of the shaft 340, and are thus not visible.

FIG. 15A illustrates the end effector 350 having an open position in which the distal tips 362r, 364r of the cutting mechanism 360 maintain some overlap between them. As the jaws 352, 354 move to a closed position, shown in FIG. 15B, distal tips 362r, 364r can become further overlapped, while the blades 362, 364 themselves can continue to be biased towards their respective upper and lower jaws 352, 354 by the leaf spring 369. In the illustrated embodiment, retention tabs 353, 355 of the jaws 352, 354 in the closed configuration can actually engage respective faces thereof, although in other embodiments, such as those provided earlier, the closed configuration can be one in which the retention tabs of the two jaws do not physically contact each other. Further, if tracks were to be formed in faces 352f, 354f of the opposed jaws 352, 354, the cutting blades 362, 364 can remain disposed in the tracks in both the open and closed positions.

Cutting Mechanism—Single Cutting Blade

Figure 16:
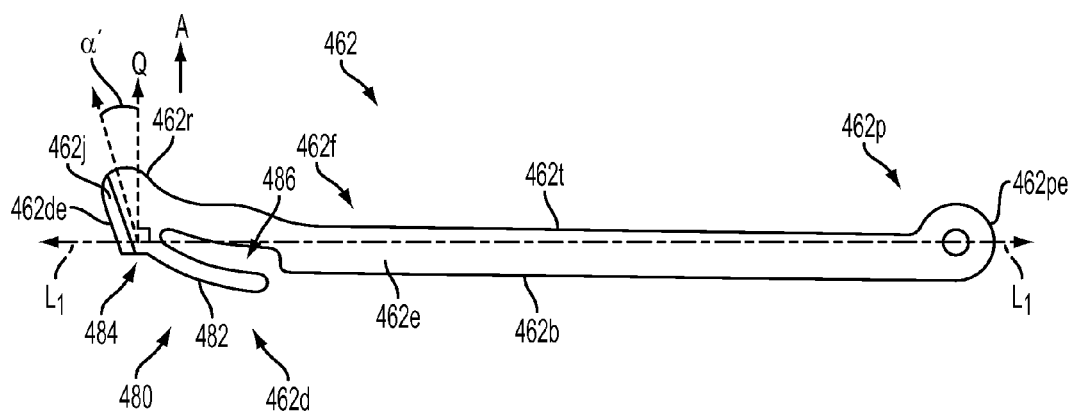
FIG. 16 is a side view of another exemplary embodiment of a cutting blade.

FIG. 16 provides for an alternative embodiment of a cutting mechanism for use in conjunction with end effectors of the nature provided for herein or otherwise known to those skilled in the art. As shown, the cutting mechanism is an elongate single cutting blade 462 defined by a proximal end 462pe, a distal end 462de, a top surface 462t, a bottom surface 462b, and opposed side surfaces 462e, 462f, the opposed side surfaces 462e, 462f forming a substantial portion of a surface area of the cutting blade 462. A proximal portion 462p of the cutting blade 462 can be configured to couple to an actuation rod associated with the handle assembly and a distal portion 462d of the cutting blade 462 can be configured to cut tissue disposed between jaws of a surgical device. The distal portion 462d can also include a biasing element, as shown a spring mechanism 480, configured to bias a distal tip portion 462f of the cutting blade 462 towards a top surface of a first jaw.

The proximal portion 462p can have any configuration that allows the cutting blade 462 to be coupled to an actuation rod that is controlled by the handle assembly. In the illustrated embodiment the proximal portion 462p is configured similar to the proximal portion 62p of the cutting blade 62 of FIG. 5, and thus it includes a lumen 462m extending therethrough that is configured to receive a pin to couple the cutting blade 462 with an actuation rod. Any other techniques known to those skilled in the art for associating a cutting blade with an actuator can also be used to allow manipulation of the handle assembly to control movement of the cutting blade 462.

The distal portion 462d can include a cutting edge 462j formed at the terminal, distal end of the cutting blade 462 and can have a configuration similar to the cutting edge 62j of the cutting blade 62 of FIG. 5. As shown, the cutting edge 462j is disposed in a substantially vertical direction, forming a small angle $\alpha'$ between a straight axis Q that extends perpendicular to the longitudinal axis $L_1$. The blade 462 also includes a rounded configuration as part of a distal tip portion 462r to allow it to easily translate through a track as it is advanced through a track formed in a jaw, as described in greater detail elsewhere herein.

The distal tip portion 462r can remain disposed in a track of a jaw, at least in part, due to the spring mechanism 480. In the illustrated embodiment, the spring mechanism 480 is formed in the distal portion 462d, adjacent to the cutting edge 462j, and is configured in a manner similar to the spring mechanism 80 of the cutting blade 62 of FIG. 5. Thus, the spring mechanism 480 can include an elongate, curved flexing arm 482 that is configured to flex or rotate about a pivot point 484 of the spring mechanism 480 to bias the distal tip portion 462r in the direction A. In the illustrated embodiment, the pivot point 484 is distal of the elongate flexing arm 482, although in other embodiments the pivot point 484 can be proximal of the elongate flexing arm 482 such that the elongate flexing arm 482 extends distally away from the pivot point 484. As shown, an elongate cut-out 486 can be formed in a portion of the cutting blade 462, extending through the opposed side surfaces 462e, 462f to form the elongate flexing arm 482. Although in the illustrated embodiments the spring mechanism 80 of the cutting blade 62 of FIG. 5 is disposed in the proximal portion 62p of the cutting blade 62 and the spring mechanism 480 of the cutting blade 462 of FIG. 16 is disposed in the distal portion 462d of the cutting blade 462, a person skilled in the art will recognize that the spring mechanisms 80, 480 can be positioned in a variety of locations along the length of the cutting blades 62, 462 without departing from the spirit of the present disclosure.

As shown in FIGS. 17-19B, when disposed in the surgical device, the elongate flexing arm 482 can be disposed against a base 454cb of a track 454c of a second jaw 454 such that it is disposed at a location that is more proximate to the second jaw 454 than a first jaw 452 of an end effector 450. The biasing interaction between the arm 482 and the base 454cb can cause the cutting blade 462 to be biased in the upward direction A, towards a base 452cb of a track 452c of the upper jaw 452. More particularly, the distal tip portion 462r can be biased in a plane that is co-planar with the page.

FIGS. 17-19B also illustrate an alternative configuration for tissue engaging surfaces 452f, 454f of the first and second jaws 452, 454. As shown, the tissue engaging surface 452f of the first jaw 452 can be substantially flat but can include a plurality of teeth 436 to assist in gripping tissue disposed between the jaws 452, 454 by increasing the friction therebetween. Likewise, the tissue engaging surface 454f of the second jaw 454 can be substantially flat but can include a plurality of grooves 438 that are complementary to the teeth 436 to assist in gripping tissue disposed between the jaws 452, 454.

Figure 17:
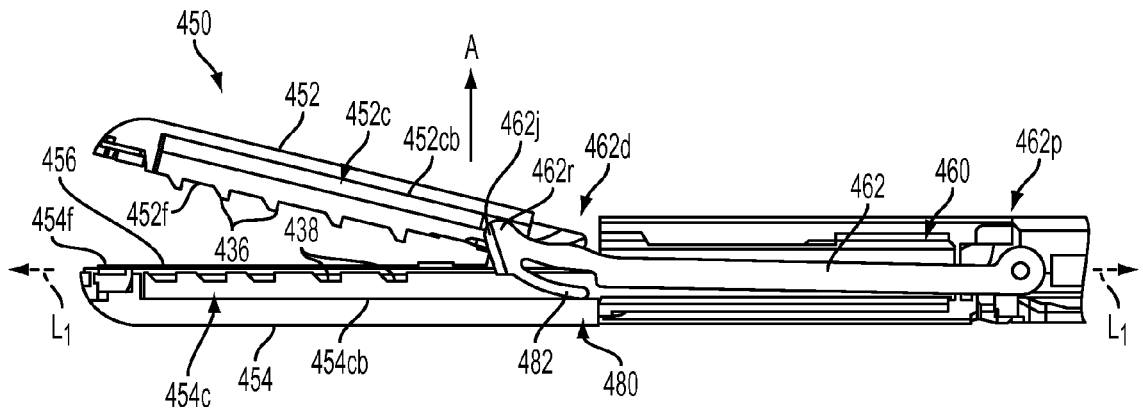
FIG. 17 is a side cross-sectional view of another exemplary embodiment of an end effector and a shaft of a surgical device, the end effector including first and second jaws disposed in an open position and the cutting blade of FIG. 16 disposed at a proximal location.
Figure 18:
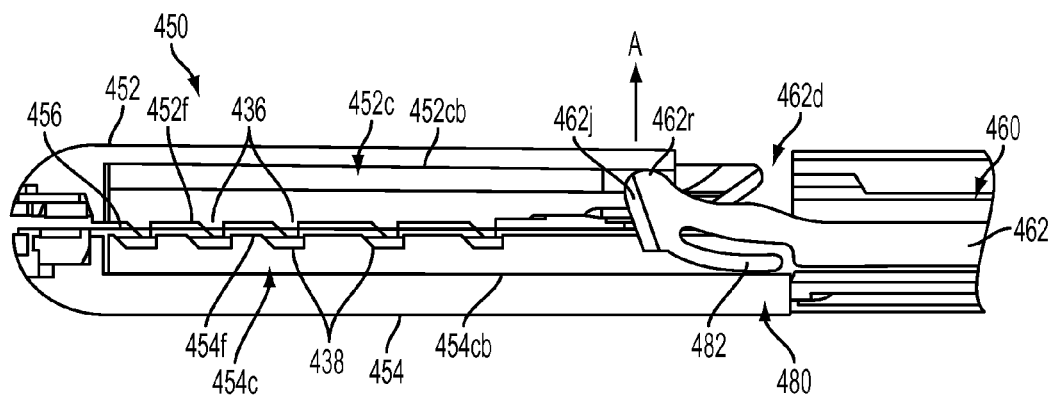
FIG. 18 is a side cross-sectional view of the jaws and cutting blade of FIG. 17, with the jaws being in a closed position and the cutting blade being at the proximal location.

In use, the spring mechanism 480 allows the vertical height of the cutting edge 462j to be greater than a distance between the tissue-engaging surfaces 452f, 454f of the first and second jaws 452, 454 at equivalent axial locations as the cutting blade 462 translates axially through a portion of the first and second jaws 452, 454. FIG. 17 illustrates the jaws 452, 454 in an open position with the cutting blade 462 being disposed in a proximal location. After the tissue or blood vessel to be transected and/or sealed is disposed in the jaws 452, 454, the handle assembly can be manipulated to move the jaws 452, 454 to the closed configuration in which tissue is engaged by the tissue-engaging surfaces 452f, 454f. The closed configuration for the jaws 452, 454 is illustrated in FIG. 18, with the cutting blade 462 remaining at its proximal location. In embodiments in which the tissue or vessel is being sealed prior to being cut, the cutting blade 462 can typically remain proximate to the proximal location so that cutting is not performed until after the sealing has at least started, or typically until it is completed. The tissue can be sealed by energy supplied though an electrode 456, the electrode 456 being operated by one or more features incorporated into the handle assembly to activate the electrode.

Figure 19A:
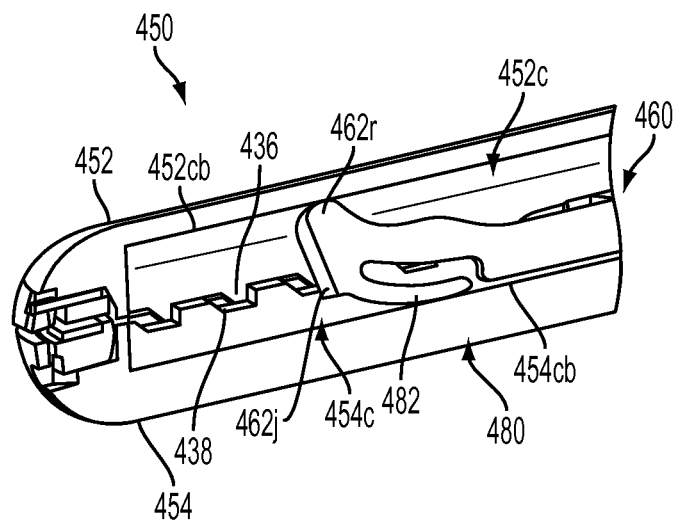
FIG. 19A is a perspective cross-sectional view of the jaws and cutting blade of FIG. 18, with the jaws being in a closed position and the cutting blade being at a more distal location.
Figure 19B:
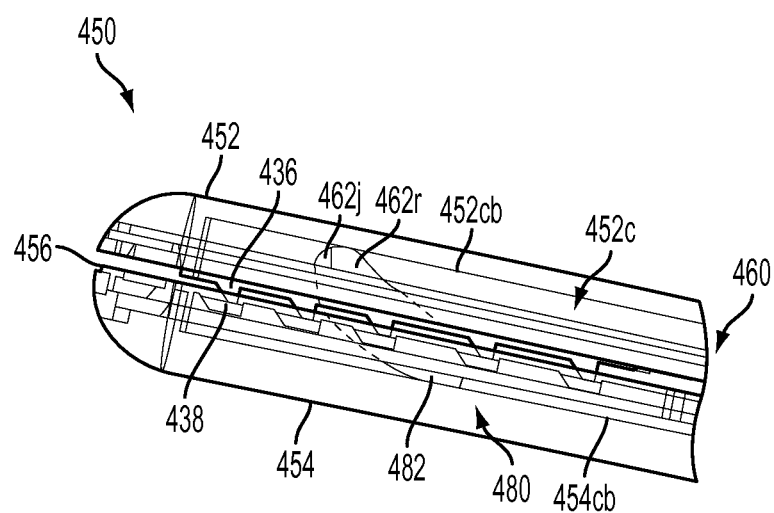
FIG. 19B is a partially transparent perspective view of the jaws and cutting blade of FIG. 19A.

As shown in FIGS. 19A and 19B, after the tissue is sealed, a cutting stroke can be performed by distally advancing the cutting blade 462 through at least a portion of the jaws 452, 454 to cut the tissue disposed between the jaws 452, 454. In embodiments in which the device is not configured to seal tissue, the blade 462 can be advanced distally any time after the jaws 452, 454 are closed. In some embodiments the blade 462 can be configured to help cam the jaws 452, 454 closed, and thus, in some embodiments the blade can be advanced while the jaws are being closed, as described elsewhere herein.

As the cutting blade 462 moves from its proximal location to its more distal location, the more distal location being illustrated in FIGS. 19A and 19B, the flexing arm 482 can remain in contact with the base 454cb of the track 454c, and the rounded distal tip portion 462r can remain in contact with the base 452cb of the track 452c during a substantial entirety of the cutting stroke. The biasing force applied to the blade 462 allows it to be self-adjusting as it translates through the jaws 452, 454, which in turn makes it difficult for the blade 462 to be displaced from or otherwise fall out of the track 452c. In other embodiments, the rounded distal tip portion 462r may extend into the track 452c but may not reach the base 452cb. Such embodiments can still be effective to allow the cutting blade 462 to cut tissue and be self-adjusting to remain disposed in the track 452c of the end effector 450 during use.

Biasing Mechanisms to Bias Cutting Blades Towards Each Other

Embodiments of a cutting mechanism that includes two cutting blades are described herein as being coupled together to maintain a location of one blade adjacent to the other, thereby forming a single continuing cutting surface. As discussed above, in some configurations the blades can be laminately restrained by a physical structure, such as a pin can disposed between the two distal ends or a clip attached to the two distal ends, or a treated surface, such as forming a highly polished surface on one or both blades, to help maintain the location of the blades with respect to each other and minimize any tissue positioning between the first and second cutting blades. In alternative embodiments, the distal ends of the cutting blades can be opposed against each other to form the single cutting surface. The resulting configuration, which is illustrated best in FIG. 21, can be one in which a distal end 562d of a second side surface 562f of the first cutting blade 562 is in contact with the a distal end 564d of a second side surface 564f of the second cutting blade 562 while an intermediate portion 562i of a first side surface 562e of the first cutting blade 562 can be disposed proximate to an intermediate portion 564i of a first side surface 564e of the second cutting blade 564. FIGS. 20-27 provide an example of a biasing mechanism that can help to create and maintain the just-described configuration in which proximal and distal ends 562p, 564p and 562d, 564 are crossed over each other but the remaining portions of the blades 562, 564, as shown intermediate portions 562i, 564i, are substantially parallel to each other.

Figure 20:
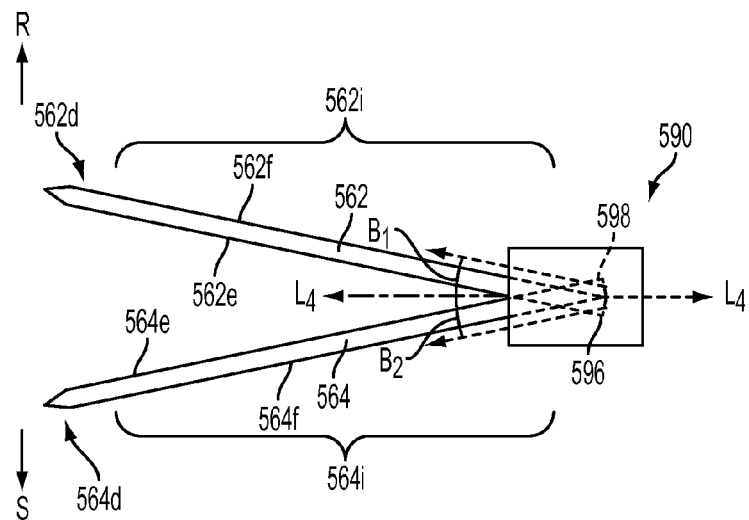
FIG. 20 is a schematic top view of one exemplary embodiment of first and second cutting blades disposed in a proximal biasing block for use in conjunction with a surgical device.
Figure 21:
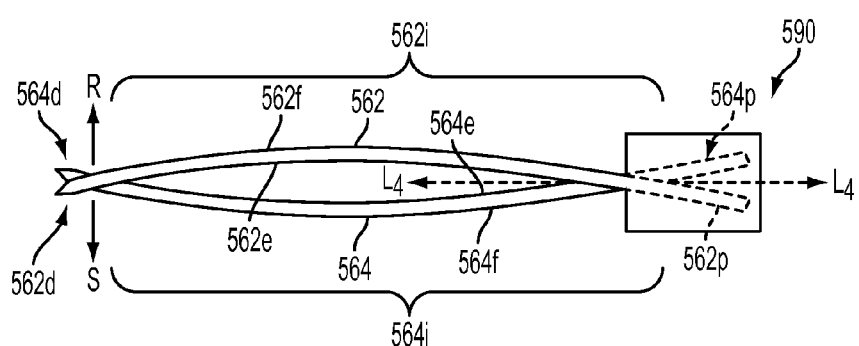
FIG. 21 is a schematic top view of the first and second cutting blades and proximal biasing block of FIG. 20, the blades having distal ends thereof hooked together.

FIGS. 20 and 21 provide a schematic illustration of one exemplary way by which the distal ends 562d, 564d of two cutting blades 562, 564 can be hooked against each other to form a single cutting surface. The resulting configuration can be incorporated into a surgical device such as the devices provided for herein or otherwise known to those skilled in the art. The two cutting blades 562, 564 can be associated with a biasing mechanism, as shown a biasing block 590, to bias the blade 562 in a direction R and the blade 564 in a direction S. As described in greater detail herein, such bias allows the distal end 562d of the side surface 562f to oppose the distal end 564d of the side surface 564f, with distal end 562d being biased in the direction R and the distal end 564d being biased in the direction S to hook the distal ends 562d, 564d together. Notably, biasing in the directions R and S occurs in a different plane than the plane in which the blades are biased in the directions A and B as described in earlier embodiments. Accordingly, the blades 562, 564 can be biased in the directions R or S and in the directions A or B in the same embodiment.

As shown in FIG. 20, proximal ends 562p, 564p of the cutting blades 562, 564 can be disposed in the biasing block 590. The biasing block 590 can be configured such that the proximal ends 562p, 564p are disposed at an angle with respect to a central longitudinal axis $L_4$ extending through the block 590, and the proximal ends 562p, 564p can cross each other such that at least a portion of the proximal end 562p is disposed more proximate to the second side surface 564f of the second blade 564 than the first side surface 564e. Likewise, at least a portion of the proximal end 564p can be disposed more proximate to the second side surface 562f of the first blade 562 than the first side surface 562e. The proximal ends 562p, 564p can be received by cam slots 596, 598 formed in the biasing block 590, as described in further detail below with respect to FIGS. 24-26. The central longitudinal axis $L_4$ can be akin to the longitudinal axis $L_1$ that extends through a shaft of a surgical instrument when this configuration is incorporated into a surgical device like the devices provided for herein or otherwise derivable from the present disclosures.

The cutting blades 562, 564 can be flexible such that the intermediate portions 562i, 564i and distal ends 562d, 564d thereof can be flexed towards each other, as shown from FIG. 20 to FIG. 21. As the intermediate portions 562i, 564i and distal ends 562d, 564d advance towards each other, the configuration of the proximal ends 562p, 564p being disposed in the biasing block 590 can impart a bias on the blades 562, 564 such that the intermediate portion 562i and distal end 562d of the first blade 562 is biased in the direction R, away from the second blade 564, and the intermediate portion 564i and distal end 564d of the second blade 564 is biased in the direction S, away from the first blade 562. However, a force can be applied to the intermediate portions 562i, 564i and/or the distal ends 562d, 564d to overcome this bias so that the distal ends 562d, 564d can be hooked together, as shown in FIG. 21. In the illustrated embodiment, the distal end 562d crosses over from a side adjacent to the first side surface 564e to a side adjacent to the second side surface 564f of the second blade 564, while the intermediate portion 562i remains more proximate to the first side surface 564e than the second side surface 564f. The distal end 562d of the second side surface 562f can then engage the distal end 564d of the second side surface 564f to hook the distal ends 562d, 564d of the two blades 562, 564 together. This configuration can be maintained by the bias supplied by the biasing block 590 because the distal end 562d continues to be biased in the direction R but is prevented from moving in that direction by the distal end 564d. Similarly, the distal end 564d continues to be biased in the direction S but is prevented from moving in that direction by the distal end 564p. Notably, although in the illustrated embodiment there is a gap between the intermediate portions 562i, 564i of the cutting blades 562, 564, in some embodiments such a gap can be minimal or even non-existent. Thus, in some embodiments, the first side surface 562e and the first side surface 564e can be adjacent to or in contact with each other.

Figure 22:
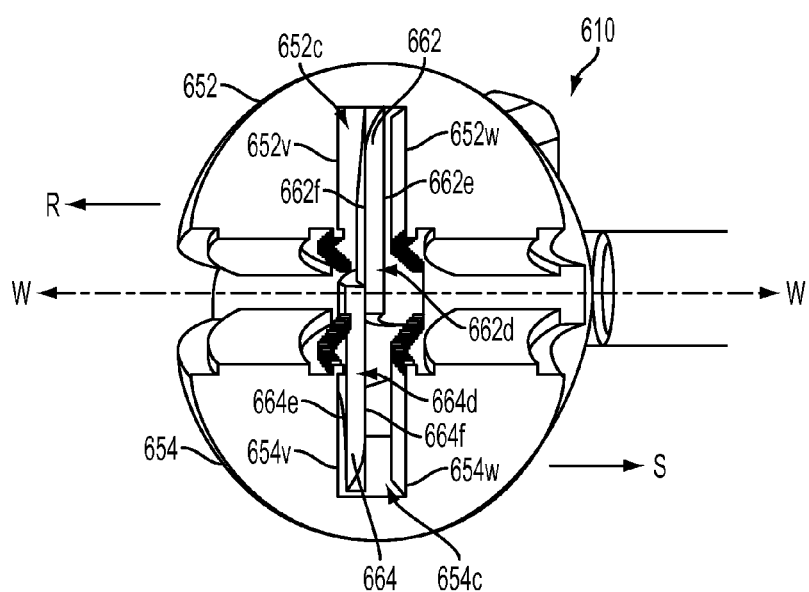
FIG. 22 is an end view of yet another exemplary embodiment of a surgical device, the device including first and second jaws, and the device further including first and second cutting blades biased in a manner as illustrated in FIGS. 20 and 21, wherein the illustrated device has a portion of the distal end of the first and second jaws removed to provide more of a cross-section illustration to more easily illustrate the first and second cutting blades.

FIG. 22 illustrates the blade configuration that results when a biasing block of the nature illustrated in FIGS. 20 and 21 is incorporated with cutting blades and jaws. More particularly, FIG. 22 provides for an end view of a surgical device 610 having a first cutting blade 662 disposed in a track 652c of a first jaw 652 and a second cutting blade 664 disposed in a track 654c of a second jaw 654. The distal ends 662d, 664d of the two cutting blades 662, 664 are hooked against each other to form a single cutting surface. In particular, the distal end 662d of the first cutting blade 662 is biased in the direction R but is prevented from going in that direction by a second side surface 654f of the second cutting blade 664. Likewise, the distal end 664d of the second cutting blade 664 is biased in the direction S but is prevented from going in that direction by a second side surface 652f of the first cutting blade 652. An intermediate portion of the cutting blade 662, however, can be disposed more proximate to a first side surface 664e than the second side surface 664f of the second cutting blade 664, and an intermediate portion of the cutting blade 664 can be disposed more proximate to a first side surface 662e than the second side surface 662f of the first cutting blade 662. This configuration of the two cutting blades 662, 664 being hooked against each other at their distal ends 662d, 664d can be maintained by a biasing block (not shown) associated with proximal ends of the cutting blades 662, 664. The biasing block can help each blade 662, 664 to be self-adjusting to maintain a location within tracks 652c, 654c of the jaws 652, 654. As shown, the first and second blades 662, 664 can be disposed substantially centrally across a horizontal axis W of the tracks 652c, 654c such that a space is maintained between first side walls 652v, 654v and second side walls 652w, 654w of the tracks 652c, 654c and the respective cutting blades 662, 664. As shown in FIG. 22, as the tracks 652c, 654c curve, the cutting blades 662, 664 can also curve to conform to the shape of the tracks 652c, 654c.

Figure 23:
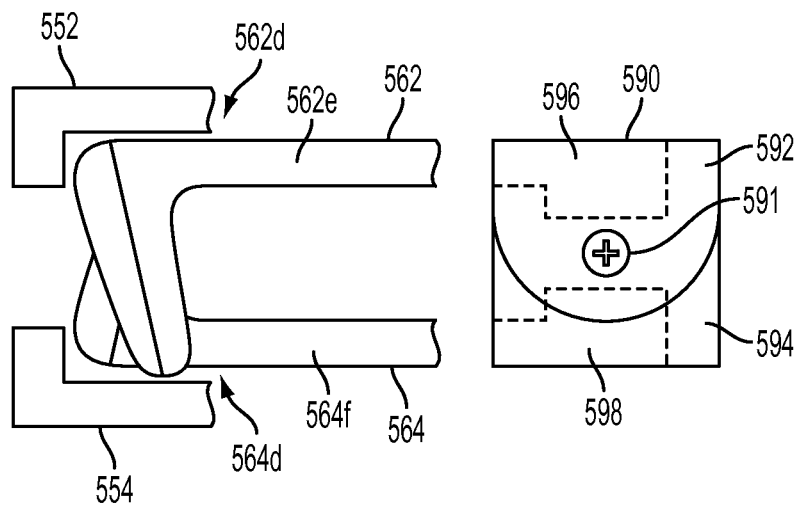
FIG. 23 is a schematic side view of the first and second cutting blades and proximal biasing block of FIG. 20.

FIG. 23 illustrates a schematic side view of the blades 562, 564 and biasing block 590 of FIGS. 20 and 21, with a portion of jaws 552, 554 against which the blades 562, 564 can also be biased towards in accordance with other disclosures contained herein also illustrated. This schematic illustration provides for only a portion of the cutting blades 562, 564, with a more proximal portion extending between the distal ends 562d, 564d and the biasing block 590 being removed for illustrative purposes. A person skilled in the art will recognize a variety of configurations that can be used to form the un-illustrated portions of the cutting blades 562, 564, as well as an un-illustrated biasing mechanism for biasing the distal ends 562d, 564d towards the respective jaws 552, 554.

Figure 24:
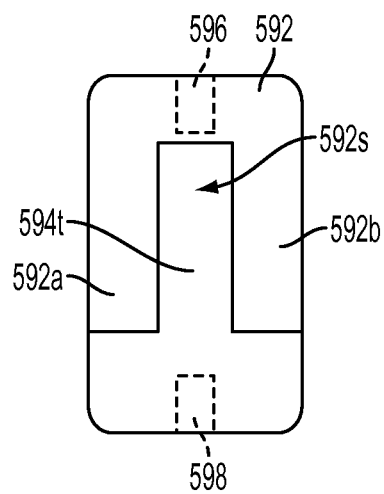
FIG. 24 is a schematic end view of the proximal biasing block of FIG. 23.

As shown in FIGS. 23 and 24, the biasing block 590 includes two receiving blocks 592, 594 that are pivotally coupled to each other. The first receiving block 592 can be configured to receive the proximal end 562p of the first cutting blade 562 in the first slot 596 and the second receiving block 594 can be configured to receive the proximal end 564p of the second cutting blade 564 in the second slot 598. The blocks 592, 594 can be complementary in shape, which as shown results in a top portion 594t of the second block 594 sitting within a slot 592s formed by first and second arms 592a, 592b of the first block 592. A pivot pin 591 can be disposed through each of the first and second receiving blocks 592, 594, thus allowing the two blocks 592, 594 to pivot with respect to each other. As shown in FIG. 23, the pivot pin 591 can be disposed substantially centrally through the two receiving blocks 592, 594 when viewed from the side. A person skilled in the art will recognize a variety of ways by which the first and second receiving blocks 592, 594 can be pivotally coupled, or otherwise associated with each other, to allow the receiving blocks 592, 594 to bias the cutting blades 562, 564 as described herein.

Figure 25:
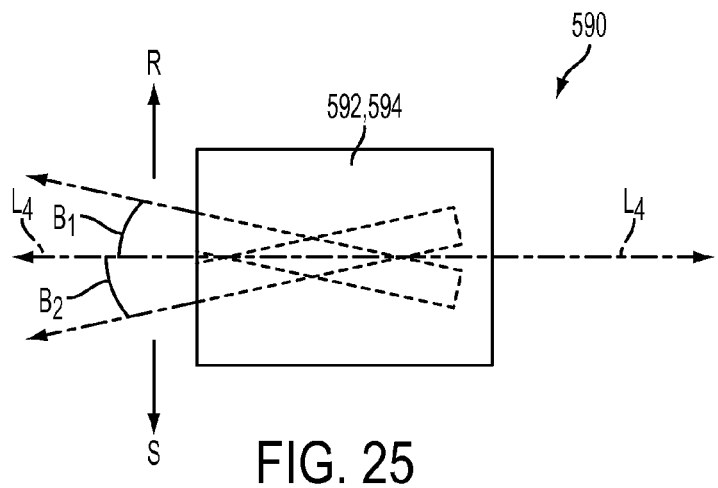
FIG. 25 is a schematic top view of the proximal biasing block of FIG. 23.
Figure 26:
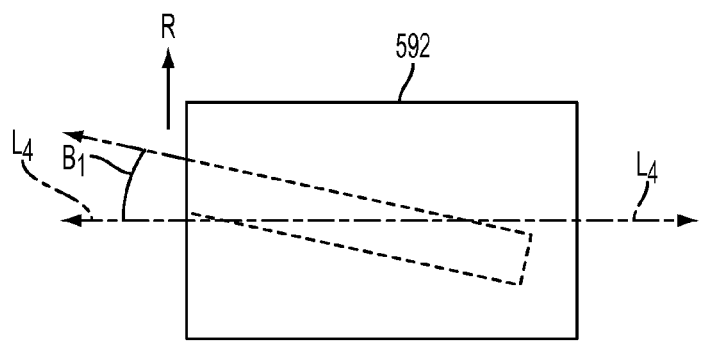
FIG. 26 is a schematic top view of a receiving block of the proximal biasing block of FIG. 25.

FIG. 25 illustrates a top view of both receiving blocks 592, 594 that form the biasing block 590. As shown, the angled slots 596, 598 are formed in the receiving blocks 592, 594, respectively, and are configured to receive proximal ends 562p, 564p of the cutting blades 562, 564. FIG. 26 provides for a clearer illustration of the angled slot because it only illustrates the first receiving block 592. An angle $\beta_1$ of the slot 596 with respect to the longitudinal axis $L_4$ can be in the range of greater than 0 degrees to about 10 degrees, and in one exemplary embodiment the angle $\beta_1$ can be about 5 degrees. An angle $\beta_2$ formed by the receiving slot 598 of the second receiving block 594 and the longitudinal axis $L_4$ can have a similar value for its angle. As shown in FIG. 25, the angled slots 596, 598 can be opposed to each other. Further, although the angles $\beta_1$, $\beta_2$ are illustrated as having the same value, in other embodiments the angles $\beta_1$, $\beta_2$ can have different values. Still further, in some embodiments, at least one of the slots 596, 598 can be approximately parallel to the longitudinal axis $L_4$.

Figure 27:
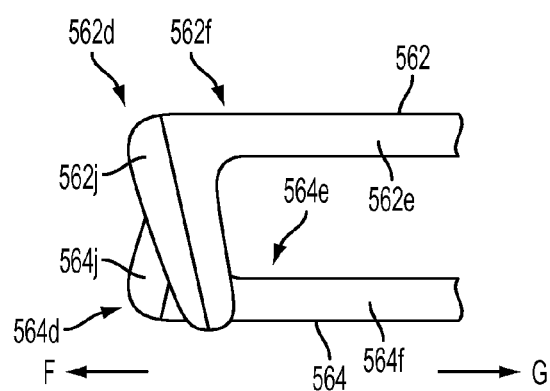
FIG. 27 is a schematic side view of distal ends of the cutting blades of FIG. 23.

After the proximal ends 562p, 564p of the cutting blades 562, 564 are disposed in the first and second receiving blocks 592, 594 such that the first cutting blade 562 is biased in the direction R and the second cutting blade 564 is biased in the direction S, and the distal ends 562d, 564d are manipulated so that the second side surface 562f of one blade 562 presses against the second side surface 564f of the other blade 564, against the biasing force imparted by the biasing block 590, the resulting configuration of the distal ends 562d, 564d of the cutting blades 562, 564 is illustrated in FIG. 27. As shown, the second side surface 562f is biased against the second side surface 564f, with the biasing block imparting a biasing force that is into the page on the first blade 562 (which is in the direction R as described herein) and a biasing force that is out of the page on the second blade 562 (which is in the direction S as described herein). The cutting blades 562, 564 can then be advanced distally in the direction F and retracted proximally in the direction G in accordance with the disclosures provided for herein or as otherwise known to those skilled in the art. As shown, the cutting edges 562j, 564j can form a single cutting surface that can be used to cut tissue as described herein.

Although in the illustrated embodiment the biasing block 590 is described as being used in conjunction with the a biasing mechanism that biases the cutting blades 562, 564 towards the jaws 552, 554 of a surgical device, in other embodiments the biasing block 590 can be used as the sole, independent biasing mechanism of a surgical device, or alternatively, it can be incorporated into any number of surgical devices that include two structures, e.g., cutting blades, configured to be biased towards each other. Further, a person having skill in the art would recognize other configurations of a biasing block that can be derived from the present disclosure. By way of non-limiting example, a biasing block can be a separation block in which proximal ends of two blades are disposed. The blades can be disposed parallel to the previously identified longitudinal axis $L_4$. The separation block can be configured to slide along the blades to bias them towards each other as previously described, and the distal ends of the blades can be maintained in manner consistent with those described herein.

One skilled in the art will appreciate further features and advantages of the invention based on the above-described embodiments. Accordingly, the invention is not to be limited by what has been particularly shown and described, except as indicated by the appended claims. For example, although the biasing elements and other features are described herein as being used in conjunction with biasing cutting blades, a person skilled in the art will recognize how these features can be incorporated into other features of surgical devices. Thus, disclosures pertaining to a flexible elongate arm can be incorporated into a surgical device to bias other tools or features other than cutting blades. Likewise, the features of one embodiment described herein can generally be incorporated into any of the embodiments provided for herein or otherwise derivable from the present disclosures. Accordingly, by way of non-limiting example, although some of the embodiments of jaws do not include tissue grasping features such as teeth and grooves, such features can be incorporated into the jaws of any of the embodiments provided for herein or otherwise derivable from the present disclosures. All publications and references cited herein are expressly incorporated herein by reference in their entirety.

What is claimed is:

1. A surgical instrument, comprising:
   a jaw assembly having a first jaw and a second jaw pivotally coupled together, the first and second jaws each having an axial channel extending through a portion thereof, and the first and second jaws being configured to engage tissue therebetween;
   a first cutting blade having a portion thereof disposed in the axial channel of the first jaw, the first cutting blade having a proximal end, a distal end, a first side surface facing in a first direction, and a second side surface facing in a second, opposite direction, the distal end being configured to cut tissue disposed between the first and second jaws;
   a second cutting blade having a portion thereof disposed in the axial channel of the second jaw, the second cutting blade having a proximal end, a distal end, a first side surface facing in the second, opposite direction, and a second side surface facing in the first direction, the distal end being configured to cut tissue disposed between the first and second jaws, wherein an intermediate portion of the first side surface of the first cutting blade is adjacent to and faces an intermediate portion of the first side surface of the second cutting blade; and
   a biasing block,
   wherein the proximal ends of the first and second cutting blades are disposed in the biasing block and the distal ends of the first and second cutting blades are hooked against each other such that the second side surface of the first cutting blade is in contact with the second side surface of the second cutting blade, and a position of the distal ends being hooked against each other being maintained by a bias supplied by the proximal ends being disposed in the biasing block.

2. The instrument of claim 1, wherein the axial channels of the first and second jaws are substantially centrally disposed with respect to a width of the respective first and second jaws, and the biasing block biases the distal ends of the first and second cutting blades such that the cutting blades are approximately centrally disposed within the axial channels of the respective first and second jaws.

3. The instrument of claim 1, wherein the biasing block further comprises:
   a first receiving block having a slot disposed therein, the slot being configured to receive the proximal end of the first cutting blade; and
   a second receiving block pivotally coupled to the first receiving block, the second receiving block having a slot disposed therein, and the slot being configured to receive the proximal end of the second cutting blade.

4. The instrument of claim 3, wherein the slot of the first receiving block extends at a first angle with respect to a central longitudinal axis extending between the first and second jaws, and the slot of the second receiving block extends at a second angle with respect to the central longitudinal axis.

5. The instrument of claim 4, wherein the first angle and the second angle have substantially the same value with the first angle extending in a first direction away from the central longitudinal axis and the second angle extending in a second direction away from the central longitudinal axis, the first and second directions being opposed to each other.

6. The instrument of claim 5, wherein the first angle and the second angle have values in the range of greater than 0 degrees to about 10 degrees.

7. The instrument of claim 1, wherein the distal ends of the first and second cutting blades overlap to form a cutting surface to cut tissue disposed between the first and second jaws.

8. The instrument of claim 1, further comprising one or more biasing elements coupled to the first and second cutting blades, the one or more biasing elements being configured to bias the first cutting blade towards a base of the axial channel of the first jaw and to bias the second cutting blade towards a base of the axial channel of the second jaw.

9. The instrument of claim 1, wherein the axial channels of the first and second jaws are curved with respect to a central longitudinal axis extending between the first and second jaws.

10. The instrument of claim 1, wherein the proximal ends of the first and second cutting blades disposed in the biasing block cross each other such that at least a portion of the proximal end of the first blade is disposed more proximate to the second side surface of the second blade than the first side surface of the second blade when viewed from a plane that is perpendicular to a plane that extends through a majority of the surface area of the first side surface of the first cutting blade.

11. The instrument of claim 10, wherein the distal ends of the first and second cutting blades cross each other such that at least a portion of the distal end of the second blade is disposed more proximate to the second side surface of the second blade than the first side surface of the second blade when viewed from a plane that is perpendicular to a plane that extends through a majority of the surface area of the first side surface of the first cutting blade.

12. A surgical instrument, comprising:
a jaw assembly having a first jaw and a second jaw pivotally coupled together, the first and second jaws each having an axial channel extending through a portion thereof, and the first and second jaws being configured to engage tissue therebetween;
a first cutting blade having a portion thereof disposed in the axial channel of the first jaw, the first cutting blade having a proximal end, a distal end, a first side surface, and a second side surface, the distal end being configured to cut tissue disposed between the first and second jaws;
a second cutting blade having a portion thereof disposed in the axial channel of the second jaw, the second cutting blade having a proximal end, a distal end, a first side surface facing in a first direction, and a second side surface facing in a second, opposite direction, the distal end being configured to cut tissue disposed between the first and second jaws, wherein an intermediate portion of the first side surface of the first cutting blade is adjacent to an intermediate portion of the first side surface of the second cutting blade, wherein the first side surface of the first cutting blade and the first side surface of the second cutting blade are facing each other; and
a biasing block,
wherein the proximal ends of the first and second cutting blades are disposed in the biasing block, the proximal ends being disposed at a non-zero angle with respect to a central longitudinal axis extending through the biasing block when viewed from a plane that is perpendicular to a plane that extends through a majority of the surface area of the first side surface of the first cutting blade, and
wherein the distal ends of the first and second cutting blades are hooked against each other such that the second side surface of the first cutting blade is in contact with the second side surface of the second cutting blade, and a position of the distal ends being hooked against each other being maintained by a bias supplied by the proximal ends being disposed in the biasing block.

13. The instrument of claim 12, wherein the biasing block further comprises:
a first receiving block; and
a second receiving block pivotally coupled to the first receiving block,
wherein the first cutting blade is disposed in the first receiving block and the second cutting blade is disposed in the second receiving block.

14. The instrument of claim 13, further comprising a pivot pin disposed through each of the first and second receiving blocks to pivotally couple the first and second receiving blocks to each other.

15. The instrument of claim 14, wherein the pivot pin is disposed substantially centrally through the two receiving blocks.

16. The instrument of claim 13, further comprising:
a first slot disposed in the first receiving block at a non-zero angle with respect to the central longitudinal axis, the first slot being configured to receive the proximal end of the first cutting blade; and
a second slot disposed in the second receiving block at a non-zero angle with respect to the central longitudinal axis, the second slot being configured to receive the proximal end of the second cutting blade.

17. The instrument of claim 13, wherein a top portion of the second receiving block sits within a slot formed by a first arm and a second aim of the first receiving block.

\* \* \* \* \*